United States Patent
Langer et al.

(10) Patent No.: US 10,081,834 B2
(45) Date of Patent: Sep. 25, 2018

(54) METHOD FOR SEQUENCING A TEMPLATE NUCLEIC ACID IMMOBILIZED ON A SUBSTRATE

(71) Applicant: DYNAMIC BIOSENSORS GMBH, Martinsried (DE)

(72) Inventors: Andreas Langer, Martinsried (DE); Ralf Strasser, Martinsried (DE); Ulrich Rant, Martinsried (DE)

(73) Assignee: DYNAMIC BIOSENSORS GMBH, Martinsried (DE)

( * ) Notice: Subject to any disclaimer, the term of this patent is extended or adjusted under 35 U.S.C. 154(b) by 180 days.

(21) Appl. No.: 14/763,078

(22) PCT Filed: Jan. 22, 2014

(86) PCT No.: PCT/EP2014/051225
§ 371 (c)(1),
(2) Date: Jul. 23, 2015

(87) PCT Pub. No.: WO2014/114665
PCT Pub. Date: Jul. 31, 2014

(65) Prior Publication Data
US 2015/0368705 A1   Dec. 24, 2015

(30) Foreign Application Priority Data

Jan. 23, 2013   (GB) .................................. 1301178.8

(51) Int. Cl.
| *C12Q 1/68* | (2018.01) |
| *C12Q 1/6869* | (2018.01) |
| *C07H 21/00* | (2006.01) |
| *C12Q 1/6825* | (2018.01) |
| *C12Q 1/6834* | (2018.01) |

(52) U.S. Cl.
CPC ......... *C12Q 1/6869* (2013.01); *C12Q 1/6825* (2013.01); *C12Q 1/6834* (2013.01)

(58) Field of Classification Search
CPC ......... C12Q 1/68; C12Q 1/6869; C07H 21/00
See application file for complete search history.

(56) References Cited

U.S. PATENT DOCUMENTS

| 7,462,452 B2 * | 12/2008 | Williams | C12Q 1/6869 435/6.1 |
| 8,399,196 B2 * | 3/2013 | Hoser | B82Y 5/00 435/6.12 |
| 2011/0312529 A1 | 12/2011 | He et al. | |
| 2011/0312830 A1 | 12/2011 | Silverbrook et al. | |

FOREIGN PATENT DOCUMENTS

| EP | 2192401 A1 | 6/2010 |
| JP | 2007531496 A | 11/2007 |
| WO | 2009056831 A1 | 5/2009 |
| WO | WO 2009/030953 | * 12/2009 |

OTHER PUBLICATIONS

Nelson et al., Surface Plasmon Resonance Imaging Measurements of DNA and RNA Hybridization Adsorption onto DNA Microarrays. Analytical Chemistry 73 :1-7 (2001).*
Shan et al., Distance-dependent quenching and enhancing of electrochemiluminescence from a CdS:Mn nanocrystal film by Au nanoparticles for highly sensitive detection of DNA . Chemical Communications (2009) : 905-907.*
Touahir et al., Localized surface plasmon-enhanced fluorescence spectroscopy for highly-sensitive real-time detection of DNA hybridization. Biosensors and Bioelectronics 25 : 2579 (2010).*
Eid et al., Real-time DNA sequencing from single polymerase molecules. Science. Jan. 2, 2009;323(5910):133-138.
Gao et al. An extension-quenching-extension sequencing on a microarray. Talanta. Apr. 15, 2010;81(1-2):418-423.
First Office Action issued by SIPO in Chinese application No. 201480005610.9 dated May 13, 2016—incl Engl lang transl.
Office Action issued by the JPO in Japanese patent application No. P2015-553131 dated May 16, 2017—incl Engl lang transl.
International Search Report and Written Opinion issued in PCT/EP2014/051225 by the ISA/EP dated Apr. 7, 2014 (10 pages).
G. Stengel, "Surface plasmon field-enhanced fluorescence spectroscopy studies of primer extension reactions", Nucleic Acids Research, 33(7):e69-e69, Apr. 11, 2005 (Apr. 11, 2005).
Spuhler et al., "Platform for in situ real-time measurement of protein-induced conformational changes of DNA", Proceedings of the National Academy of Sciences, 107(4):1397-1401, Jan. 26, 2010 (Jan. 26, 2010).

* cited by examiner

*Primary Examiner* — Ethan C Whisenant
(74) *Attorney, Agent, or Firm* — TechLaw LLP; Sam K. Tahmassebi

(57) ABSTRACT

The present invention is directed to sequencing of nucleic acids. A method is provided for sequencing based on immobilized nucleic acid on a surface. Advantageously, a long range detection mechanism is used for detecting, whether a nucleotide provided to the substrate of a biochip has been incorporated into the immobilized template nucleic acid. Various different alignment means are provided by the present invention which can be used for facilitating a rigidly locking of the orientation of the DNA complex, which complex comprises the template nucleic acid, the primer and the capture nucleic acid. Various different linker systems may be used to immobilize the DNA complex at a first and a second strand end, such that the desired alignment of the DNA complex is achieved. Also co-adsorbed molecules on the substrate surface can be used for such an aligning measure. Additionally, or alternatively, an electrical field may be applied for repelling the DNA complex from the electrode and for facilitating a vertical DNA complex orientation. Advantageously, label-free nucleotides can be used, if desired.

15 Claims, 8 Drawing Sheets

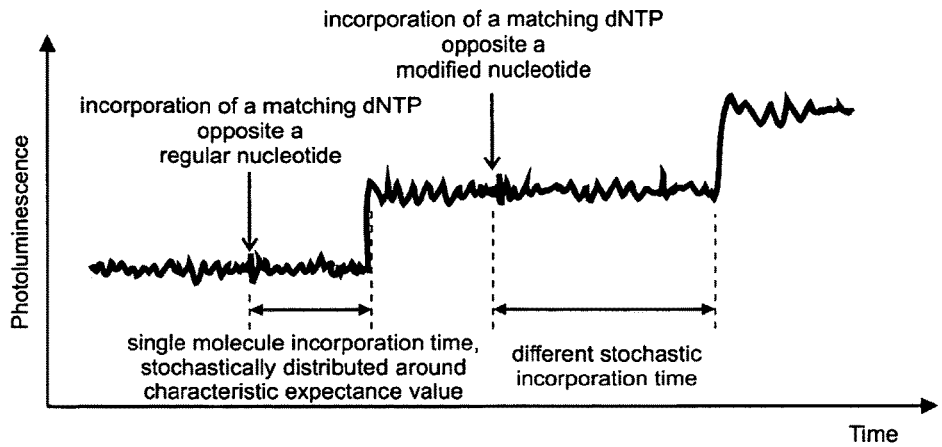
Fig. 8
3′ HS-(CH$_2$)$_6$- [20nt, mixed sequence] - [22bp primer region 8 ] - TTT-Cy3
5′ HS-(CH$_2$)$_6$- [20nt, complem. seq.] - [20bp compl. primer ]
Fig. 9a
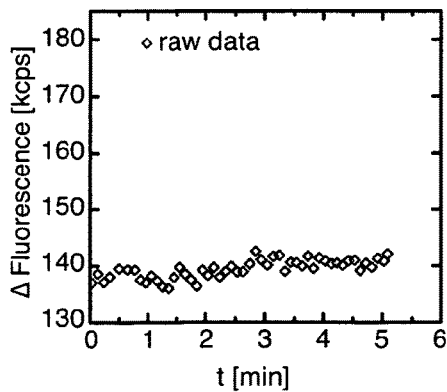
Fig. 9b
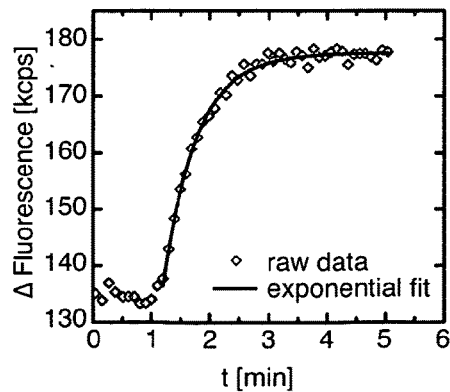
Fig. 9c 3' HS-(CH$_2$)$_6$- [42nt, mixed seq.] - TTT CTC ACT ACA TTG GTC-Cy3
3' HS-(CH$_2$)$_6$- [40nt, compl. seq.] - AAA
Fig. 10a
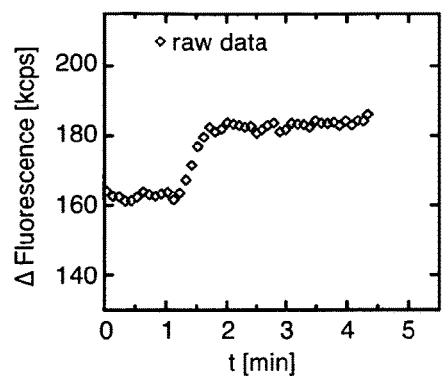
Fig. 10b
3' HS-(CH$_2$)$_6$- [18nt, mixed seq.] CGT ATT TCT CAC TAC ATT GTC CTA TTT-Cy3
5' HS-(CH$_2$)$_6$- [18nt, compl. seq.] GC
Fig. 11a
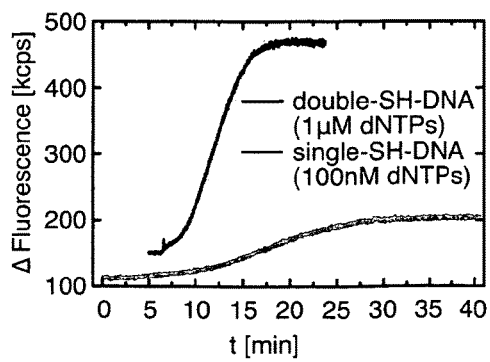
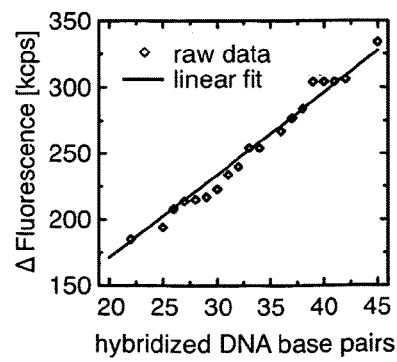
Fig. 11b  Fig. 11c

METHOD FOR SEQUENCING A TEMPLATE NUCLEIC ACID IMMOBILIZED ON A SUBSTRATE

CROSS REFERENCE TO RELATED APPLICATIONS

The present invention is filed under 35 U.S.C. § 371 as the U.S. national phase of International Application No. PCT/EP2014/051225, filed Jan. 22, 2014, which designated the U.S. and which claims benefit of priority to Great Britain Patent Application No. 1301178.8, filed Jan. 23, 2013, each of which is hereby incorporated in its entirety including all tables, figures, and claims.

FIELD OF THE INVENTION

The present invention relates to nucleic acid sequencing. In particular, the present invention relates to a method for sequencing a template nucleic acid immobilized on a substrate, a program element for sequencing a template nucleic acid, a computer-readable medium, a vessel for sequencing a template nucleic acid, a use of a vessel for sequencing a template nucleic acid, and to a sequencing apparatus for sequencing an immobilized template nucleic acid.

BACKGROUND OF THE INVENTION

Nucleic acid sequencing such as DNA sequencing is the process of determining the precise order of nucleotides within a DNA molecule. It includes any method or technology that is used to determine the order of the four bases—adenine, guanine, cytosine, and thymine—in a strand of DNA. The advent of rapid DNA sequencing methods has greatly accelerated biological and medical research and discovery. Knowledge of DNA sequences has become indispensable for basic biological research, and in numerous applied fields such as diagnostic, biotechnology, forensic biology, and biological systematics. The rapid speed of sequencing attained with modern DNA sequencing technology has been instrumental in the sequencing of complete DNA sequences, or genomes of numerous types and species of life, including the human genome and other complete DNA sequences of many animal, plant, and microbial species.

The first DNA sequences were obtained in the early 1970s by academic researchers using laborious methods based on two-dimensional chromatography. Following the development of fluorescence-based sequencing methods with automated analysis, DNA sequencing has become easier and orders of magnitude faster.

However, many sequencing methods rely on ensemble measurements and cannot be carried out on a single DNA molecule basis. Furthermore, most currently used sequencing methods entail a labeling of the nucleotides which are incorporated into the template DNA strand, which leads to certain disadvantageous during the sample preparation and the measurement itself. Further, the need for labeled dNTPs used for sequencing increases the costs. Moreover, a part of the state of the art sequencing methods make use of pyrophosphate for the generation of a detection signal, which however is relatively insensitive.

SUMMARY OF THE INVENTION

There may be a need to provide for an improved sequencing of a template nucleic acid. In particular, there may be a need for a sensitive sequencing with unlabeled dNTPs.

The object of the present invention is solved by the subject-matter of the independent claims. Further embodiments and advantages of the invention are incorporated in the dependent claims.

The embodiments of the present invention described hereinafter in more detail similarly pertain to the method for sequencing a template nucleic acid, the program element for sequencing a template nucleic acid, the computer-readable medium, the use of a vessel for sequencing the template nucleic acid and the sequencing apparatus for sequencing a template nucleic acid. Synergetic effects may arise from different combinations of the embodiments, although they might not be described hereinafter explicitly.

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plurality of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

The term "nucleic acid" refers to any type of nucleic acid molecule that can be sequenced such as DNA or RNA or PNA or LNA or any polymer that consists of a sequence of chemical units. DNA is a preferred nucleic acid. The term "nucleic acid template" refers to any type of nucleic acid molecule that is to be sequenced. DNA templates are preferred nucleic acid templates. With the presented methods, DNA templates with bases in length between 5 and 10000 or more can be sequenced. For example, templates may have up to about 10000, up to 5000, up to 1000, up to 900, up to about 800, up to about 700, up to 500, up to about 250, up to about 100, up to about 50 bases in length. DNA templates will typically be at least 5 bases in length.

It is to be understood that for the purposes of the present invention, that the term "nucleic acid template" and "DNA template" refer to at least partially and preferably completely single stranded nucleic acid sequences and single stranded DNA sequences as this pre-requisite for sequencing. In combination with a capture nucleic acid and/or a primer nucleic acid, the resulting complex may comprise a single-stranded part and a double-stranded part.

The term "nucleotide" as used herein encompasses any desoxyribonucleotide and encompasses any 2'-deoxynucleoside-5-triphosphate (dNTP) as they are used during sequencing. The term "nucleotide" thus includes dNTPs such as dATP, dGTP, dCTP and dTTP, and any derivatives thereof. As used herein, the term "nucleotide" refers to any one selected from the group consisting of mononucleotides, oligonucleotides, and polynucleotides, and mixtures thereof. Such substances are often negatively charged. Use may be made of a single-stranded and/or double-stranded nucleotide. Moreover, it is possible for protein, DNA, and nucleotides to be intermingled. Biopolymers include not only those originating from living organisms, but also those modified from bio-polymers originating from living organisms, and synthesized molecules.

The term "primer" and/or "nucleic acid primer" refers to a nucleic acid and preferably DNA sequence of typically at least 6 bases in length, for which the sequence is known and which can be annealed with a template nucleic acid and preferably a DNA template. The length of these primers will be typically have 5 to 100 bases in length to allow for efficient annealing with a nucleic acid template and preferably a DNA template. But other primer lengths are also possible. Primers will thus have a free OH-group at their 3'-end.

The term "polymerase" refers to an enzyme which can elongate the 3'-end of a primer that has annealed to a nucleic acid template. DNA polymerases are preferred. DNA polymerase may preferably provide for proof-reading activity. Any of the commercially available DNA polymerases may be used. A preferred DNA polymerase is Bst DNA polymerase from *Bacillus stearothermophilus*. However, also other polymerases may be used without departing from the present invention.

The "label" as used herein may be any suitable entity capable of emitting a signal. The signals in this case may include any physical signals, chemical signals, or biological signals. Of these, electromagnetic waves may be preferred. A photoluminescent label that emits photoluminescence when excited by the excitation of electromagnetic waves, particularly light, may be especially preferred. In particular, fluorescent and phosphorescent labels may include fluorescent dyes, metals, and semiconductor nanoparticles.

Further, the number of labels on a complex is not subject to any particular limitation and may be suitably selected according to the intended purpose. The number is at least one, and may be two or more. The position of the label on the complex is not subject to any particular limitation, and may be suitably selected according to the intended purpose.

In cases where the complex, as defined in the following, is linear, possible label positions include the ends thereof. If the complex is a polynucleotide or includes a polynucleotide, the label position may be e.g. at the 3'-end or at the 5'-end. Other positions are also possible. Depending the specific embodiments contemplated and described hereinafter, the label may be associated covalently or non-covalently with a complex as described hereinafter. In preferred embodiments, a label, which may preferably be photoluminescent label, is associated with the polymerase used in the sequencing method and/or with the template nucleic acid. In these cases a covalent attachment is preferred. Even though the label may also be attached to the dNTPs used during sequencing, a preferred embodiment of the invention considers label-free dNTPs.

Furthermore, hereinafter the term "complex" will be used as a description of a combination of molecules. A complex, as used herein, at least comprises the template nucleic acid and the primer nucleic acid. However, also additional molecules may be comprised. For example, the complex comprises the template nucleic acid, the primer nucleic acid and the polymerase. Therefore, in the context of the present invention, the term "complex" can be described synonymously with the term "DNA complex" or "DNA/polymerase complex". Moreover, a preferred complex in accordance with the invention is a combination of a nucleic acid template, a primer, a polymerase and any other type of molecule or molecules such as a capture oligonucleotide that is used to attach the nucleic acid template to the substrate. Said molecules for attaching may be termed "binding unit" herein. As will be explained in detail hereinafter, the binding unit may be embodied in various different ways. The complex may also be termed "lever" or "DNA-lever" hereinafter. Furthermore, since the term "complex" and the term "binding unit" are not limited to any specific shape, this terminology is rather metaphorical, and should not be understood to impose any restriction on the type or shape of the complex and or the binding unit. Further, instead of DNA, also RNA can be used in the context of the present invention.

The template nucleic acid may be immobilized on the substrate by adhesion and/or cohesion forces. However, a more preferred embodiment makes use of a binding unit which binds the template to the substrate such that the immobilization is achieved. The binding unit can consist of or can comprise a capture nucleic acid. Moreover, the term "binding unit" will be used hereinafter as follows. The binding unit may be embodied, for example, as a chemical linker for binding the template nucleic acid to the substrate. Examples of such linkers will be given hereinafter. Alternatively, the binding unit may be embodied as a capture nucleic acid for binding the template nucleic acid to the substrate. However, also a combination of a chemical linker and a capture nucleic acid is a possibility to realize the binding unit. Various different other possibilities of immobilizing entities the template nucleic acid at the substrate are encompassed by the term "binding unit". A variety of examples will be explained in more detail in the context of FIG. 1 in the following.

The term "covalently or non-covalently associated with the template nucleic acid" will be used hereinafter in the sense of comprising a direct or an indirect attachment to the template nucleic acid. For example, the label may be attached to the polymerase which itself is attached to the template nucleic acid. The label may be covalently or non-covalently bound to the template nucleic acid, e.g. by way of a labeled polymerase-specific antibody. However, a label like for example a photoluminescent label may also be attached to the end of the template nucleic acid, or may also be attached to the capture/primer oligonucleotide. Further, also the term "attached to the complex" and "attached to the template nucleic acid" will be used hereinafter in the sense of comprising a direct or an indirect attachment, respectively. For example, the label may be attached to the polymerase which itself is attached to the complex. However, a label may also be attached to the end of the template nucleic acid, or may also be attached to the capture/primer oligonucleotide which is part of the binding unit.

According to an exemplary embodiment of the invention, a method for sequencing a template nucleic acid immobilized on a substrate, wherein a label is covalently or non-covalently associated with the template nucleic acid, wherein a nucleic acid primer is annealed to said template nucleic acid, wherein a quenching medium for quenching a signal of the label is provided. The method comprises at least the steps of a) adding a nucleotide,
b) determining whether said nucleotide is incorporated or not incorporated at a 3'-end of said nucleic acid primer annealed to said template nucleic acid by:
observing a signal of the label at least before and after the adding of the nucleotide, using the observed signal of the label for detecting an incorporation of the nucleotide into the template nucleic acid based on a change of the observed signal of the label, and wherein the change of the signal results from a change of a distance of the label to the quenching medium caused by the incorporation of the nucleotide into the template nucleic acid.

According to a further exemplary embodiment the quenching medium is a quenching layer.

In another exemplary embodiment the quenching layer may be provided on the substrate, as will be explained in more detail hereinafter. However, in other embodiments, the quenching layer is not located on the substrate. The previously mentioned embodiments relating to the quenching layer may be used in combination with each other embodiment comprised herein unless mentioned to the contrary. Particularly, also in the embodiments relating to a program element, a computer-readable medium, a vessel, a use of a vessel and/or a sequencing apparatus the quenching medium can be embodied as a quenching layer, e.g. on the substrate.

The presented sequencing method comprises the step of detecting an incorporation of a nucleotide into the template nucleic acid based on a change of a signal emitted by a label. Furthermore, the change of the signal results from a change of a distance of the label to the substrate, which change of distance is caused by the incorporation of the nucleotide into the template nucleic acid. This will be described hereinafter in more detail and may be gathered from, for example, FIGS. 1 to 12.

The presented method provides for an increased precision and reliability of sequencing a template nucleic acid. Advantageously, unlabeled nucleotides, dNTPs, can be used. Thus, nucleotide incorporation by the polymerase is not affected/hindered by the chemical tag and native processivity is retained. Moreover, the approach is cost-effective because it makes the expensive labeling of nucleotides obsolete. Moreover, the presented method allows for single molecule sequencing. Using, for example, photo-stable PL-labels which are resistant to photobleaching, the described approach can be used to monitor nucleotide incorporation at the single molecule level with commercially available optical instrumentation. In addition to improved efficiency and faster workflows, this offers the important opportunity to investigate epigenetic modifications. In particular, the methylation state of nucleotides along a DNA template can be inferred from the measured incorporation time of the matching nucleotide. By contrast, conventional, prior art sequencing schemes require the amplification of template DNA via a PCR process, during which the methylation state of the original DNA strand is disadvantageously lost. By the herein presented method the nucleotide incorporation rate can be measured in real-time, which is impossible with most sequencing systems on the market. In doing so, different nucleotides along the template strand can be discriminated according to the different processivity of a given polymerase to incorporate the matching dNTP from solution and move on to the next base on the template. Advantageously, nucleotides which are chemically modified—e.g., which have been methylated during an epigenetic process or damaged (oxidized, etc.) in some other way—can be identified by the herein presented method and apparatus for sequencing. Moreover, the incorporation time provides information on the length of nucleotide repeats, i.e. stretches of the same nucleotide, on the template, which generally are difficult to quantify with established methods. However, the herein presented method and apparatus match this need. Furthermore, the polymerase association and dissociation rate to/from the template and primer DNA can be measured when using a labelled polymerase. These aspects of the presented method and apparatus will be explained in more detail hereinafter.

Furthermore, the presented method facilitates the use of a quenching mechanism, provided by a quenching medium like e.g. a quenching layer on the substrate, which allows for a non-radiative energy transfer from the label to the quenching medium. The combination of the label used and the quenching medium used may be chosen, in this and every other embodiment of the present invention, such that a non-radiative energy transfer from the excited label to surface plasmons in the quenching medium quenches the emission of the signal of the label, when the label approaches the quenching medium, and vice versa. From a physical point of, the following should be noted. An applied bias to said quenching medium polarizes the quenching medium, e.g. the electrode 107 of FIG. 1, leading to the formation of a Gouy-Chapman-Stern screening layer. Non-radiative energy transfer from the label to surface plasmons in the quenching layer may quench the emitted signal intensity when the label approaches the surface in a distant dependent manner. Therefore, high signal intensities indicate a large distance of the label from the quenching medium, which in this case functions as the quenching medium. Low signal intensities indicate a close distance of the label from the quenching medium. This will become apparent from and will be elucidated with, for example, FIGS. 1 to 12.

Thus, the presented method may be seen as a method for detecting, e.g. optically, an incorporation of a single nucleotide by changing the distance between the quenching medium and the label. The photoluminescent signal change may be recorded during the method or by the apparatus of the present invention, and may facilitate the determination of an nucleotide incorporation event. Consequently, the herein presented method may be seen as a method for sequencing a template nucleic acid based on the incorporation of unlabelled nucleotides.

In exemplary embodiments, the present invention makes use of an energy transfer mechanism which is very long ranged in order to measure the distance between the label above the quenching medium over hundreds of nanometers. Usually, in the prior art, researchers are used to employ "fluorescence resonance energy transfer" (FRET, also called Förster resonance energy transfer) to measure molecular distances optically. Conventional FRET occurs from a donor to an acceptor molecule and has a typical range of 10 nm only. In contrast thereto, we devised a scheme where the acceptor can be implemented as a two-dimensional quenching layer. This modality features a conceptually different, exceptionally long-ranged energy transfer distance dependence. This leads to an improved sequencing as will be explained in the following.

In a specifically developed embodiment, the presented method may be seen as a method for detecting the incorporation of a nucleotide based on a distance-dependent quenching. Various aspects about the quenching and appropriate quenching means will be disclosed and explained hereinafter. In particular, the method may make use of a combination of a quenching medium and a label, such that the absorption spectrum of the quenching medium coincides to some extend with the emission spectrum of the label. The combination can be chosen such that a non-radiative energy transfer is facilitated. The quenching mechanism used by the presented method might be seen as a continuous process or interaction between the quenching medium and the label which is provided over a long distance. Such a long distance interaction may be present between at least 0 and 300 nanometres. A quenching mechanism, which is also effective over a longer distance, can be used. The quenching mechanism can be selected to be sensitive in the range of 0.2 to 0.4 nanometres. This facilitates a detection of the incorporation of a single nucleotide into the template nucleic acid.

It will be understood by the person skilled in the art that the quenching medium may be embodied as a quenching layer. The quenching layer may be embodied as a thin layer, e.g. as an electrically conducting electrode, which can have a low thickness. Due to the low thickness such a quenching medium can be called two dimensional quenching layer hereinafter. The thickness can be, for example, between 5-300 nm. This layer can be provided on the substrate and may facilitate the use of a quenching mechanism by a non-radiative energy transfer from the label to the quenching layer. Also a mono-atomic layer could be used. The combination of the label used and the quenching layer used may be chosen such that a non-radiative energy transfer from the excited label to surface plasmons in the quenching layer quenches the emission of the signal of the label, when the label approaches the quenching layer, and vice versa. The quenching layer can thus be configured to be polarized by an applied bias leading to the formation of a Gouy-Chapman-Stern screening layer. As a non-limiting example for the quenching layer the electrode 107 of FIG. 1 can be supplied with a DC or AC bias such that the electrode is polarized and the interaction of the label and the surface plasmons can take place. Exemplary variations of such a quenching layer will be given in detail hereinafter.

In an exemplary embodiment the label is a photoluminescent (PL) label and the quenching medium is a metal layer on the substrate of the biochip. The used quenching effect can chosen to be sensitive regarding the distance of the photoluminescent label to the metal layer in the range of 0.2 to 0.4 nanometres. However, also other sensitivities are possible. Generally, the base pair spacing of DNA or RNA is 0.34 nanometres. The present invention makes use of a shift of the label due to incorporation of a nucleotide in this range, i.e. 0.34 nanometres. As will become clear from and elucidated with the following explanation, the photoluminescence intensity increases or jumps for a characteristic, predetermined value in case one nucleotide is incorporated. Based on such characteristic, predetermined value, the presented method can optically detect whether the type of nucleotide provided to the substrate in e.g. a solution is complementary to an upcoming unpaired nucleotide along the template DNA next to a single-stranded/double-stranded junction.

Another valuable aspect of the presented method is that both single molecule measurements as well as ensemble measurements comprising a plurality of template DNA molecules are facilitated. In said single molecule measurement, only one template nucleic acid is used. This may be gathered from, for example, FIGS. 1*a*, 1*b*, 5 and 6. In said ensemble measurements, a plurality of template nucleic acids with a respective nucleic acid primer annealed thereto may be provided on the substrate or on different substrates. As will be explained in more detail hereinafter, the incorporation of only one nucleotide is detectable by the presented method and apparatus for sequencing in both measurements, the single molecule and the ensemble molecule measurements. In the ensemble sequencing configuration a complex layer comprising a plurality of complexes is provided. In the following the present invention will mostly be explained in the context of the single molecule configuration. However, also a plurality of complexes may be sequenced simultaneously by the present invention. In this respect, we will refer hereinafter to such configurations by using the term "DNA layer" or "DNA layers".

Further, the presented method may be seen as a method for being used in sequencing. Some repetitions or additional steps might be supplemented to completely determine the sequence of the template nucleic acid. Such repetitions and additional method steps will be described in more detail hereinafter.

During the sequencing with the presented method, label-free nucleotides, for example dATP, dCTP, dGTP, and/or dTTPs, and any derivative thereof, can be sequentially exchanged above the surface of the substrate, while the signal intensity of the label can be recorded in real-time. The incorporation of a matching nucleotide along the template DNA by the polymerase is detected as an increase in signal intensity, because the label moves away from the quenching medium. As the double-stranded part of the DNA becomes elongated, this results in an increase of distance of the label to the substrate and the quenching medium. As will be described hereinafter, advantageously, matching nucleotides can be discriminated from mismatched nucleotides. Also modified, for example methylated or damaged nucleotides on the template can be identified. Nucleotide incorporation rates and association/dissociation rates of the polymerase on the template nucleic acid can be determined.

As the user of the method and the sequencing apparatus knows which type of nucleotide, e.g. dATP, dGTP, dTTP or dCTP, is added to the substrate at a given point in time during the sequencing, the complementary nucleotide in the template nucleic acid can be determined, if an incorporation event is detected. However, as will be explained in more detail hereinafter, also a plurality of nucleotides may be provided in a solution to the substrate, wherein they may be of the same type, and may also be of different types.

In general, the signal may be seen as the signal intensity, or a derivative thereof. In other words, the method of the present invention may be seen as a feedback in form of a signal intensity with respect to the distance between the label and the quenching medium.

By virtue of special linkers, and/or co-adsorbed molecules, and/or an applied electrical field in DC mode, the template nucleic acid can be rigidly aligned to a desired orientation on the surface, like e.g. a quasi-vertical orientation. However, such an advantageous alignment is only optional, and will be described with more detailed explanations hereinafter.

Further, the step of observing a signal of the label at least before and after the adding of the nucleotide may be carried out by first observing the signal before the addition of the nucleotide and the second after the addition. However, also a continuous observation is comprised by this method step, as shown in e.g. FIG. 3. Thus, also the signal of the label before, after and during the addition is encompassed. As an exemplary embodiment a continuous, time-resolved observation, detection and/or record of the signal of the label is presented.

In this and every other exemplary embodiment a capture nucleic acid may be used to bind the template and the primer to the substrate or the electrode. Therein the capture nucleic acid may be a double stranded capture nucleic acid having a first strand end and a second strand end. This will explained in more detail hereinafter.

It should be noted that single strand immobilization, i.e. immobilizing the DNA template at one strand only is encompassed by the present invention. The template nucleic acid, the primer and also the capture nucleic acid may be immobilized to the substrate at only one strand. If a connection to the substrate can be established which is rigid enough with respect to the motional degree of freedom of the DNA, this can be sufficient for carrying out the present invention. Thus, also in this case the user can be provided with a very sensitive sequencing method. Such a single strand immobilization may be achieved, for example, by chemically amending one end of a strand of the template or the capture oligo and/or by means of attaching an appropriately chosen chemical linker to establish a binding to the substrate. However, in a preferred embodiment, both ends of the complex with the template and the primer are bound via both strands to the substrate as shown in FIGS. 1a and 1b. In particular, in case a capture nucleic acid is used, said capture oligo can be bound to the substrate via both of its strands. In case only a primer and a template nucleic acid are used without a capture nucleic acid, the present invention comprises that the resulting double strand can be bound to the substrate via one strand only or via both strand ends, whatever the user prefers.

The method presented herein is carried out by the skilled person at an appropriate temperature. An appropriate exemplary temperature range can be between 4° C. and 80° C. to achieve the desired sequencing. However, other ranges may be used. In particular, the used/applied temperature may be optimized and chosen based on the used polymerase. As different polymerases may be used, the applied temperature may vary. The temperature may also be chosen such that the used primer remains hybridized to the template.

According to another exemplary embodiment, so called "50% populations" of double stranded capture nucleic acids are provided. Therein, 50% of the capture nucleic acids are bound to substrate at/via the longer strand and the remaining 50% of the capture nucleic acids are bound to substrate at/via the shorter strand.

This may provide for the advantage, that the effect of the rotation cancels out and one observes a net height increase of the base pair spacing, approximately the 0.34 nm*sin α, with α being the angle to the surface. This avoids the disadvantage that, if the DNA is not completely vertically aligned, for certain nucleotide additions the net increase in Δh can vanish or become negative while for others it becomes more than 0.34 nm. Hence, this embodiment may provide for an improved signal quality.

According to another exemplary embodiment of the invention, the method further comprises the step repeating steps a) and b) to determine a full sequence of said template nucleic acid.

As indicated before, the determination whether or not the nucleotide is incorporated, i.e. the detection of the incorporation event, may be embodied, for example, as an optical detection of an amended photoluminescence (PL) signal of a PL label.

According to another exemplary embodiment of the invention the nucleotide is unlabeled.

According to another exemplary embodiment of the invention, the step of immobilizing the template nucleic acid on the substrate via a capture nucleic acid is presented.

Therein, the capture nucleic acid may be seen as a binding unit. The capture nucleic acid reduces the DNA's motional degrees of freedom, which has advantages for the determination of the incorporation event, as will be described herein. By immobilizing the template nucleic acid on the substrate via the capture nucleic acid, an alignment is carried out which may lead to an improved detection of the signal emitted by the label.

According to another exemplary embodiment of the invention, the capture nucleic acid is a double-stranded capture nucleic acid having a first strand end and a second strand end. The method further comprises the step of immobilizing the double-stranded capture nucleic acid on the substrate by means of a first chemical linker at the first strand end and by means of a second chemical linker at the second strand end.

As already explained with respect to the previous embodiment, also this immobilization step leads to an alignment of the template nucleic acid which is bound to the substrate via the capture nucleic acid. This may be seen, for example, in FIG. 1a and FIG. 1b. Both previously described embodiments ensure that a template nucleic acid alignment is appropriately and rigidly locked, and that the orientation can be chosen to be almost vertical with respect to the surface of the substrate. If desired, additional alignment means may be applied by the present invention.

Additionally, e.g. a linker system can be chosen so as to reduce the DNA's motional degrees of freedom even stronger. Thus, a structurally rigid connection can be established between the DNA and the surface.

According to another exemplary embodiment of the invention, the method further comprises the step of aligning the capture nucleic acid in a desired angular configuration with respect to the surface of the substrate by applying a force onto the capture nucleic acid.

In particular, aligning means may be provided such that the capture nucleic acid is provided in a vertical direction. This may further improve the signal quality of the presented sequencing method. Therein, aligned may be seen as fixed, hold, kept spatially constant, in for example a vertical direction. Also combined forces may be used which sum up to a total force applied on the capture nucleic acid, for example by applying a DC voltage and co-adsorbed molecules, as will be described in more detail hereinafter.

According to another exemplary embodiment of the invention, the alignment of the capture nucleic acid is vertical.

Therein, the term "vertical" may be seen as substantially vertical or in a near-vertical direction. Deviations from an exact 90° orientation of the template nucleic acid may be allowed in this embodiment of the present invention. In particular, the term "vertical direction" shall be interpreted in relation to the substrate. Therefore, a perpendicular orientation of the capture nucleic acid to the surface of the substrate are achieved by the described aligning measures.

According to another exemplary embodiment the method comprises the step of applying a DC voltage or an AC voltage to the quenching layer. The quenching layer may thus be seen as an electrode. The voltage may be applied between the quenching layer/electrode on the substrate and between a counter electrode as will be described hereinafter in more detail.

According to another exemplary embodiment of the invention, the force onto the capture nucleic acid is provided by applying a DC voltage between an electrode on the substrate and a counter electrode.

This embodiment can be gathered from, for example FIGS. 1a and 1b, and will be described in more detail later on.

According to another exemplary embodiment of the invention, the method further comprises the step of applying co-adsorbed molecules on the substrate beside the capture nucleic acid for sterically repelling the template nucleic acid and/or the capture nucleic acid.

An exemplary application of co-adsorbed molecules can be gathered from for example FIGS. 1a and 1b, in the context of which different embodiments for co-adsorbed molecules will be disclosed.

According to another exemplary embodiment of the invention, the method comprises the steps of providing the label at a height h1 at the template nucleic acid; incorporating the nucleotide into the template nucleic acid, thereby causing a change of the height of the label from a height h1 to a height h2 above the quenching medium. Furthermore, the step of recording the change of the signal of the label based on the change from the height h1 to the height h2 is comprised.

In other words, the incorporation the nucleotide into the template and at the 3'-end of the nucleic acid primer annealed to said template nucleic acid is based on the observed signal, which is indicative for the change of the height from h1 to h2. For example, this may be done by the calculation unit 122 shown in FIG. 1. Thus, the method and the sequencing apparatus of the present invention allow for a detection of a height change of the label based on a characteristic signal change. For this purpose, a characteristic value of the change of the signal may be stored, for example in the sequencing apparatus, like for example in the calculation unit. The change of the height may be an increase, as shown in FIG. 1. However, a decrease of the height is also comprised by the present invention, in particular by this exemplary embodiment. In case a quenching layer is positioned on, beside or close to the electrode 114, a decrease of the signal would have to be expected. In case h2 is larger than h1, less quenching is present at height h2 in the embodiment of FIG. 1, such that more signal intensity is emitted at h2. In case h2 is smaller than h1, more quenching is provided such that less signal intensity is emitted. The quenching medium may also be positioned at distant locations from the electrode, for example as a layer on the counter electrode.

According to another exemplary embodiment of the invention, the method comprises the step of quenching an emission of the label, i.e. quenching the signal of the label.

In particular, this encompasses a partial quenching in the sense of a distance-dependent continuous quenching. Generally, this embodiment facilitates the change of an amount of the quenching rate upon the incorporation of a nucleotide, thereby changing the signal generated by the label, which is observed and detected by the presented embodiment/invention. This may also comprise the step of increasing quenching of a photoluminescent signal and the decreasing of said signal upon incorporating the nucleotide. If desired, a quenching medium may be part of the substrate, but may also be comprised as a separate component. For example, the DNA complex, i.e. the template nucleic acid, the primer and the capture nucleotide, may be immobilized on the substrate, whereas the quenching medium may be located on a second substrate which may be positioned distantly from the first substrate. For example, the quenching medium may also be positioned on the counter electrode. Furthermore, instead of a complete layer, also a layer with recessions may be used. Moreover, also molecules may be used as quenching medium, which molecules are configured to quench the signal of the respective label in a distance-dependent manner.

In the embodiment of FIG. 1, the quenching is performed by a quenching layer on the substrate, wherein the quenching layer is configured to quench the emission of the photoluminescent label in a distance-dependent way, i.e. in a height-dependent way.

According to another exemplary embodiment of the invention, the quenching is reduced upon the incorporation of the nucleotide into the template nucleic acid thereby increasing the signal which is emitted by the label.

Due the caused elongation of the DNA complex upon incorporation of the dNTP which is added to the DNA complex on the substrate, the signal is increased as the amount of quenching is decreased. The presented embodiment/invention advantageously employs this mechanism for sequencing.

According to another exemplary embodiment of the invention, the method further comprises the steps of determining a time-averaged signal emitted by the label, and the step of comparing the time-averaged signal with a signal of a point in time before the incubation was initiated is comprised. Moreover, deciding whether the nucleotide has been integrated into the template nucleic acid or not, based on a result of the comparison is carried out.

This embodiment may be of particular use when the label is attached to the template nucleic acid, in particular attached to the end of the template nucleic acid, as shown in, for example, FIG. 1b. More details about this configuration and such a measurement will be explained hereinafter at full length.

According to another exemplary embodiment of the invention, the method comprises the following steps: incubating the substrate with a solution containing a plurality of nucleotides of a first type, incorporating a nucleotide of the solution into the template nucleic acid in a first case, in which the first type is complementary to an upcoming unpaired nucleotide along the template nucleic acid next to a single-stranded/double-stranded junction, in the first case detecting an increase of the signal due to the incorporation of the nucleotide or, in a second case, in which the first type is not complementary to the upcoming unpaired nucleotide, detecting an unchanged signal, and repeating the previous steps with a different type of nucleotide.

According to an exemplary embodiment of the invention, the method further comprises the step of determining a nucleotide incorporation rate or a nucleotide incorporation time, based on a time development of the signal emitted by the label during the incorporation of the nucleotide.

In other words, based on the real-time detection of the signal emitted by the label during the incorporation, both or only one parameter of the nucleotide incorporation rate and the nucleotide incorporation time may be calculated by the presented method. For example, the determined nucleotide incorporation rate may be used to identify which type of nucleotide the incorporated nucleotide is. This embodiment may be carried out in an ensemble measurement, but may also be carried out in a single-molecule measurement.

According to another exemplary embodiment of the invention, the method further comprises the step of comparing the determined nucleotide incorporation rate with a default nucleotide incorporation rate, and/or comparing the determined nucleotide incorporation time with at least one default nucleotide incorporation time. Based on said comparison or comparisons, the step of determining the type of the nucleotide can be carried out by this embodiment.

For example, the calculation unit 122 may carry out said steps. But other different components, like an external server may alternatively carry out said steps. Further aspects of this embodiment will be described in connection with the following FIGS. 7 and 8.

According to another exemplary embodiment of the invention, the method further comprises the step of comparing the determined nucleotide incorporation time with at least one default nucleotide incorporation time, and or comparing the determined nucleotide incorporation time with at least one default nucleotide incorporation time, and determining a chemical state of the template nucleotide, for example a methylated state of the template nucleotide, based on a result of the comparison of the nucleotide incorporation times.

In particular in single molecule measurements, this embodiment of the present invention facilitates to identify whether a nucleotide of the template nucleic acid is modified, like for example methylated or damaged. Therefore, the methylated state of the template nucleic acid can be determined with the presented method. Disadvantageously, prior art sequencing methods necessarily rely on ensemble measurements and a polymerase chain reaction (PCR) has to be used. Unfortunately, the methylated state of the template DNA or template RNA is lost during PCR. Advantageously, this embodiment of the present invention provides for the possibility to gain information about the state of the template nucleic acid, as the comparison of the nucleotide incorporation times can be done on a single molecule level. Hence, this embodiment of the present invention avoids a PCR and can detect whether the template is methylated or not, based on the result of the nucleotide incorporation times. In case the measured or determined nucleotide incorporation time significantly deviates from the default nucleotide incorporation time, it is detected that the state of the template at the current complementary nucleotide changed from its natural state.

According to another exemplary embodiment of the invention, the method is carried out on a chip. Furthermore, the step of incubating the chip with a solution comprising a plurality of nucleotides of a first kind is comprised, and the step of gauging a length of a homo-nucleotide stretch along the template nucleic acid based on the determined nucleotide incorporation rate is comprised.

Also this embodiment may be carried out on a single molecule measurement basis.

According to another exemplary embodiment of the invention, a program element for sequencing a template nucleic acid immobilized on a substrate is presented, which program element, when being executed by a processor, is adapted to carry out: using data of a signal of the label, which signal was observed at least before and after an addition of the a nucleotide, determining whether said nucleotide is incorporated or not incorporated at a 3'-end of said nucleic acid primer annealed to said template nucleic acid, wherein the determining is based on a change of the observed signal of the label, and wherein the change of the signal results from a change of a distance of the label to the quenching medium caused by the incorporation of the nucleotide into the template nucleic acid. According to a further exemplary embodiment the quenching medium is a quenching layer.

A program element may be part of a computer program, but it can also be an entire program by itself. For example, the computer program element may be used to update an already existing computer program to get to the present invention. For example, the program element may be stored on the calculating unit of the sequencing apparatus.

According to another exemplary embodiment of the invention, a computer-readable medium, on which a computer program for sequencing a template nucleic acid immobilized on a substrate is stored, is presented. The computer program, when being executed by a processor, is adapted to carry out: using data of a signal of the label, which signal was observed at least before and after an addition of the a nucleotide, determining whether said nucleotide is incorporated or not incorporated at a 3'-end of said nucleic acid primer annealed to said template nucleic acid, wherein the determining is based on a change of the observed signal of the label, and wherein the change of the signal results from a change of a distance of the label to the quenching medium caused by the incorporation of the nucleotide into the template nucleic acid. According to a further exemplary embodiment the quenching medium is a quenching layer.

The computer-readable medium may be seen as a storage medium, such as for example a USB stick, a CD, a DVD, a data storage device, a hard disc, or any other medium, in which a program element as described above can be stored.

According to another exemplary embodiment of the invention, a vessel for sequencing a template nucleic acid immobilized on a substrate of the vessel and for facilitating a detection of an incorporation of a nucleotide into the template nucleic acid by facilitating a quenching of a signal of a label is presented. The vessel comprising the substrate, the template nucleic acid, the label, wherein the label is covalently or non-covalently associated with the template nucleic acid, wherein the template nucleic acid is immobilized on the substrate, and the vessel further comprising a quenching medium for quenching the signal of the label. According to a further exemplary embodiment the quenching medium is a quenching layer.

If desired, such a vessel may be seen as a biochip or a simple substrate which complies with the requirements and features defined before. An exemplary embodiment of such a vessel can be gathered from FIG. 1 in which the vessel 119 is shown. Such a vessel may be received by a sequencing apparatus upon insertion, such that the combination of the biochip and the apparatus can carry out the embodiment of the method as described before and in the following. According to another exemplary embodiment of the invention, the vessels is a biochip.

According to an exemplary embodiment of the invention, the vessel comprises a double-stranded capture nucleic acid having a first strand end and a second strand end, wherein the double-stranded capture nucleic acid is immobilized on the substrate by means of a first chemical linker at the first strand end and by means of a second chemical linker at the second strand end.

This embodiment of the vessel ensures that the template nucleic acid alignment is rigidly locked and that the orientation is almost vertical with respect to the surface of the vessel. This embodiment is shown in FIG. 1 and provides certain advantages as described above and as will become apparent from explanations in the following.

According to another exemplary embodiment of the invention, the vessel may comprise alignment means for aligning the capture nucleic acid in a desired angular configuration in relation to the surface.

The alignment means of the vessel may be configured to apply a force onto the capture nucleic acid for aligning the capture nucleic acid. If desired, the capture nucleic acid is aligned in a vertical direction on the vessel. The alignment means may be embodied as an electrode on the substrate and a counter electrode. Alternatively or additionally, the alignment means may be embodied as co-adsorbed molecules on the substrate of the vessel beside the capture nucleic acid so that the template nucleic acid and/or the capture nucleic acid is sterically repelled. This may improve the signal quality for the presented sequencing purposes.

According to another exemplary embodiment of the invention, the use of a biochip according to one of the previously described vessel embodiments is presented, wherein the biochip is used for sequencing a template nucleic acid immobilized on the substrate of the biochip. According to a further exemplary embodiment the quenching medium is a quenching layer.

According to another exemplary embodiment of the invention, a sequencing apparatus for sequencing a template nucleic acid immobilized on a substrate is presented. The sequencing apparatus is configured for receiving a vessel with a substrate on which the template nucleic acid is immobilized and with a label covalently or non-covalently associated with the template nucleic acid, wherein the substrate comprises a quenching medium for quenching a signal of the label. Further, a nucleic acid primer is annealed to said template nucleic acid. The sequencing apparatus comprises detection means for observing a signal of the label, a calculation unit configured for determining whether a nucleotide is incorporated or not incorporated at a 3'-end of said nucleic acid primer annealed to said template nucleic acid. Therein, the calculation unit is configured for carrying out said determination based on a change of a signal which was observed at least before and after an addition of the a nucleotide to the substrate. Furthermore, the change of the signal results from a change of a distance of the label to the quenching medium caused by the incorporation of the nucleotide into the template nucleic acid. According to a further exemplary embodiment the quenching medium is a quenching layer.

In other words, the calculation unit is configured to identify from a comparison of a first signal observed before the addition of the nucleotide and a second signal observed after the addition of the nucleotide, where a change of the signal, which is characteristic for an incorporation of the nucleotide, is present. Also one signal from a continuous measurement can be used. Such a characteristic value may be termed Δ hereinafter. If a characteristic increase Δ or decrease Δ of the signal intensity is detected, an incorporation event can be recorded by the sequencing apparatus. Alternatively, a signal may be generated by the apparatus indicating that an incorporation event has been detected.

The herein presented sequencing apparatus is configured to carry out the different method embodiments described herein unless stated differently.

An exemplary embodiment of a sequencing apparatus according to the present invention is shown in FIG. 1 with reference sign 120. The calculation unit may be configured for identifying an incorporation event from data received by the calculation unit from the detection means of the apparatus. The calculation unit may be configured to detect the incorporation based on the principles explained with respect to the following FIGS. 3, 7, 8, 9, 10, 11, and 12. This aspect will be explained in more detail hereinafter. The detection means may be embodied as a detector, like for example a photo-detector, and further embodiments will be described later-on. The calculation unit may be a processor or a CPU but may also be embodied differently. Moreover, the sequencing apparatus can be calibrated, for example, with respect to the characteristic value Δ by a known template and by means of an observation of the incorporation of one or more known nucleotides.

According to another exemplary embodiment of the invention, the sequencing apparatus comprises a receiving section for receiving a biochip on which the template nucleic acid is immobilized on a substrate of the chip. Further, in incubation module configured for sequentially exchange solutions with label-free nucleotides above the surface of the biochip is comprised.

By means of the exemplary embodiment, different sequential quenching steps can be carried out with different nucleotides. In particular, this embodiment may be configured to carry out the incubation and readout steps, as described above in the section "sequencing steps".

According to another exemplary embodiment of the invention, the detection means are configured to record in real-time the signal of the label during the sequential exchange of solutions on the biochip. Such a real-time recording carried out by an apparatus of the present invention can be gathered from FIGS. 3, 7, 8, 9, 10, and 11, respectively.

According to another exemplary embodiment of the invention, the sequencing apparatus comprises a DC voltage source, wherein the DC voltage source is for aligning a capture nucleic acid in a desired angular configuration in relation to the surface of the substrate.

In other words, the DC voltage source may be seen as alignment means, as has been described before and hereinafter with respect to aligning the template nucleic acid, preferentially in an approximately vertical orientation.

It may be seen as the gist of the invention to provide for a sequencing method based on immobilized nucleic acid sequencing on a surface. Advantageously, a long range detection mechanism is used for detecting, whether a nucleotide provided to the substrate of a biochip has been incorporated into the immobilized template nucleic acid. Various different alignment means are provided by the present invention in order to facilitate a rigidly locking of the orientation of the DNA complex, which complex comprises the template nucleic acid and the capture nucleic acid. Various different linker systems may be used to immobilize the DNA complex at a first and a second strand end, such that the desired alignment of the DNA complex is achieved. Also co-adsorbed molecules on the substrate surface can be used for such an aligning measure. Additionally, or alternatively, an electrical field may be applied for repelling the DNA complex from the electrode and for facilitating a vertical DNA complex orientation. In exemplary embodiments the quenching medium is embodied as a quenching layer and is made out of an electrically conductive material and is located on a substrate. These and other features of the invention will become apparent from and be elucidated with reference to the embodiments described hereinafter. Advantageously, label-free nucleotides can be used, if desired.

BRIEF DESCRIPTION OF THE D WINGS

Exemplary embodiments of the invention will be described in the following drawings.

FIGS. 1a and 1b schematically show two sequencing apparatuses according to two exemplary embodiments of the invention.

FIG. 2 shows a voltage response of a 40 base pair DNA layer and describes the principle of the quenching mechanism used by exemplary embodiments of the present invention.

FIG. 3 schematically shows photoluminescence increase upon nucleotide incorporation according to an exemplary embodiment of the invention.

FIG. 4 shows a flow diagram of a sequencing method according to an exemplary embodiment of the invention.

FIGS. 5 and 6 schematically show sequencing of a template nucleic acid according to two exemplary embodiments of the invention.

FIG. 8 shows a photoluminescence signal recorded during nucleotide incorporation on a single molecule level according to an exemplary embodiment of the invention.

FIG. 9 schematically show incubation of a surface-immobilized double-stranded DNA sequence with a 3-nucleotide single-stranded overhang with mismatching dNTPs and matching dNTPs according to an exemplary embodiment of the invention.

FIG. 10 show the incorporation of a single dNTP during a sequencing method according to an exemplary embodiment of the invention.

FIG. 11 schematically show polymerisation of a 25 nt single-stranded segment along a 45 nt DNA sequence by incubation with a mixture of all 4 dNTPs, i.e. FIG. 11b, or the sequential incubation with matching dNTPs, i.e. FIG. 11c according to an exemplary embodiment of the invention.

FIG. 12 schematically shows sequencing analogues to FIG. 11c with a DNA which is tethered with one linker only according to an exemplary embodiment of the invention.

In principle, identical parts are provided with the same reference symbols in the figures.

DETAILED DESCRIPTION OF EMBODIMENTS

Figure 1A:
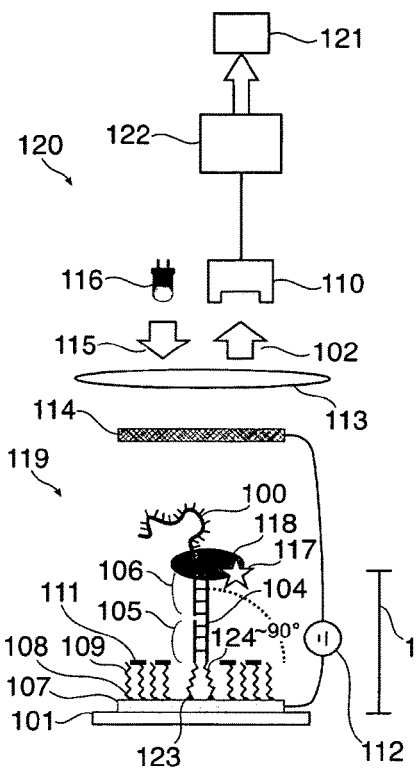
Figure 1B:
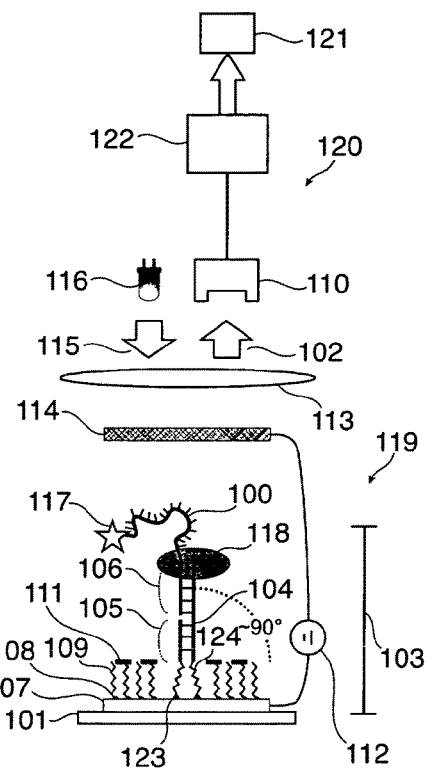

FIG. 1a and FIG. 1b respectively show a sequencing apparatus 120 for sequencing a template nucleic acid 100 immobilized on a substrate, wherein a label 117 is indirectly attached to the template nucleic acid 100 in FIG. 1a and is directly attached to the template nucleic acid in FIG. 1b. In FIG. 1a the label 117 is bound to the polymerase 118 and is thus indirectly attached to template 100. The nucleic acid primer strand 104 is annealed to the template 100. The sequencing apparatus 120 of both FIGS. 1a and 1b comprise detection means 110 for detecting a signal of the label, and a calculation unit 122 configured for detecting an incorporation of a nucleotide into the template nucleic acid based on a change of the detected signal. Therein, the change of the signal results from a change of a distance of the label to the substrate caused by the incorporation of the nucleotide into the template nucleic acid. A vessel 119 for sequencing a template nucleic acid is received by the apparatus 120 via a receiving section of the apparatus. Also, the detection means 110 may be configured to record in real-time the signal of the label during a sequential exchange of solutions on the vessel. The apparatus may comprise an incubation module (not shown) configured for sequentially exchange solutions with label-free nucleotides above the surface of the vessel 119. The excitation energy is depicted with sign 115 and the signal which is emitted by label 117 and which is observed, detected and/or recorded is shown in FIGS. 1a and 1b with sign 102. FIGS. 1a and 1b both show the distance 103 of the label to the quenching medium 107. The quenching medium is provided as a quenching layer.

A change of said distance 103 can be detected by the presented sequencing apparatus 120 as a change of the signal 102, in particular as a significant increase or decrease of the intensity of the signal 102. Therefore, change of the distance 103 of the label 117 to the quenching medium 107 caused by the incorporation of a nucleotide (501 or 601 in FIGS. 5 and 6) into the strand comprising the template nucleic acid 100 and the primer 104 is detected. The corresponding elongation process of the DNA strand upon incorporation, causing a change of the height of the label 117 above the quenching medium 107 from a first height h1=h (n) to a second height h2=h (n+1) can easily be gathered from FIGS. 5 and 6. As can be gathered from both FIGS. 1a and 1b, the respective primer nucleic acid strands 104 and capture strands attached thereto are aligned nearly vertical with respect to the substrate 101 and the electrode 107 which functions as a quenching medium 107. This vertical alignment can be achieved in various ways, as has been described before and will be exemplified in more detail hereinafter. Said alignment may improve the signal and/or the may simplify the step of detecting the incorporation event, i.e. using the observed signal 102 of the label 117 for detecting an incorporation of the nucleotide into the template nucleic acid based on a change of the observed signal (102) of the label.

From a physical point of, the following should be noted. An applied bias polarizes the electrode 107, leading to the formation of a Gouy-Chapman-Stern screening layer. Non-radiative energy transfer from the label to surface plasmons in the quenching layer may quench the emitted signal intensity when the label approaches the surface in a distant dependent manner. Therefore, high signal intensities indicate a large distance of the label from the electrode, which functions here as the quenching medium. Low signal intensities indicate a close distance of the label from the electrode. This will become apparent from and will be elucidated with, for example, FIGS. 2, 3, 5 and 6.

Figure 5:
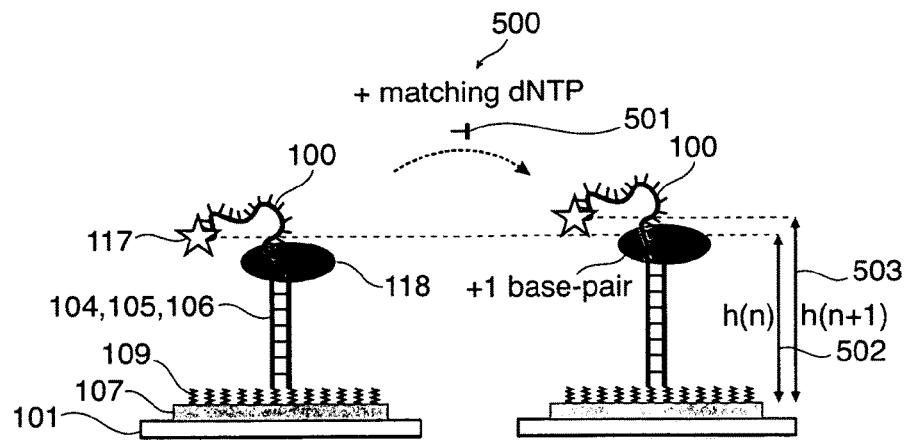
Figure 6:
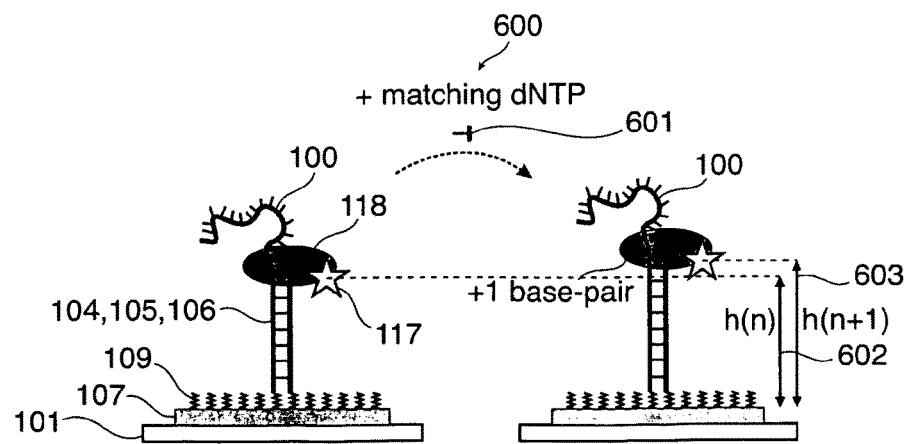

As has been described before, the vessels 119 and sequencing apparatuses 120 shown in FIGS. 1a and 1b facilitate and carry out a method for sequencing the template nucleic acid 100 immobilized on the substrate 101, wherein the label 117 is covalently or non-covalently associated with the template nucleic acid 100. The nucleic acid primer 104 is annealed to said template nucleic acid. The vessels 119 and sequencing apparatuses 120 facilitate the addition of nucleotide and the determination whether said nucleotide is incorporated or not incorporated at a 3'-end of said nucleic acid primer annealed to said template nucleic acid 100. Therein, observing the signal 102 of the label 117 at least before and after the adding of the nucleotide is carried out. Moreover, the observed signal of the label is used for detecting an incorporation of the nucleotide into the template nucleic acid based on a change of the observed signal 102 of the label. For example, this may be done by calculation unit 122. Further, the change of the signal results from a change of the distance 103 of the label 117 to the quenching medium 107 caused by the incorporation of the nucleotide into the template nucleic acid 100. If desired, the apparatus 120 may be configured to repeat the previously described step to determine a full sequence of said template nucleic acid 100. Preferably, the nucleotide is unlabeled. Please note, that a nucleotide, which is incorporated into the template 100 and the primer 104 by the polymerase 118, is depicted in FIGS. 5 and 6 with signs 501 and 601.

Apart from the general concept of the present invention explained before with respect to FIGS. 1a and 1b, a plurality of exemplary, further developed embodiments of the present invention will be explained in this context of FIGS. 1a and 1b. Therefore, in the following it is referred to both figures by using the term "FIG. 1". Hence, various embodiments of the method, apparatus and vessel for carrying out the present invention are presented for the skilled person. Consequently, the features described in the following may easily be applied isolated from other features described therein, unless explicitly stated to the contrary.

The experimental setup of FIG. 1 may be amended to integrate the following features. In FIG. 1 a non-conducting solid-phase substrate 101, which may be out of e.g. glass or plastic, serves as a flat support for a quenching-layer and for the working-electrode 107. Optionally, the quenching layer may simultaneously serve as an electrode. The quenching-layer 107 consists of an energy-accepting material that suppresses the light emission of a photoluminescence emitter 117 when said emitter approaches the layer. In a preferred embodiment, the quenching layer can be metal layer, in particular a gold film of 5-300 nm thickness. Also an organic layer, e.g. a conducting polymer or a dye-sensitized matrix, may be used. The absorption spectrum of the quenching layer should coincide to some extent with the emission spectrum of the PL-emitter, so that non-radiative energy transfer is facilitated. The PL emitter 117 can be an organic dye molecule or a nanoparticle. It may be either attached to the polymerase (FIG. 1a), or attached to the DNA template strand (FIG. 1b). In the latter case, the PL emitter 117 may be covalently bound to the template strand 100 as indicated in FIG. 1b, or alternatively, a short oligonucleotide carrying one or several PL-marker(s) can be hybridized to the template strand (not shown in FIG. 1). PL-emission is stimulated by excitation light 115 from a light source 116 which is collimated onto the surface by imaging optics 113 or laser deflection optics 113. For the detection of PL light, imaging optics 113 and a photo-detector 110 can be used. If desired, the detection may be spatially resolved. For the optional application of electric fields, the quenching-layer, which then may function as a working-electrode 107 is connected to a counter electrode 114 via a voltage source 112. Negative voltages may be applied to the electrode in order to electrostatically repel negatively charged DNA. The use of electric fields to facilitate a vertical DNA orientation is described herein as an embodiment of aligning means. The working and the counter electrodes may be integrated in a fluidic compartment filled with electrolyte solution (not shown). The solution above the surface may be exchanged by some form of a liquid handling device, for instance a pump connected to a microfluidic channel, or (automated) pipetting procedures (not shown). The previously described elements may be used as components of the sequencing apparatus 120.

The DNA template strand to be sequenced 100 is bound to the surface by hybridizing to a primer nucleic acid 104 via a dedicated primer/adapter region 106. Furthermore a capture oligonucleotide is comprised. The surface-near part of the primer/capture strand forms a rigid DNA duplex with a shorter reinforcement oligonucleotide strand 105. The primer/capture strand is fixated at one end by a chemical linker 124, 123, which may form a relatively strong covalent bond to the surface. For instance, a sulfur—gold bond may be used. The reinforcement oligonucleotide strand 105 is also fixated to the surface via a dedicated linkers 123, 124. Strands 105 and 106 may be separate strands that may—or may not—be joined by a ligase. The use of linkers which confer structural rigidity in order to efficiently align the DNA vertically is an advantageous measure to provide for a reliable and improved sequencing. This can be accomplished by using two or more linkers, or a singular chemical structure which is especially designed for structural integrity and rigidity such that the desired restriction or constraint of the degree of freedom of the template and the primer, i.e. the DNA, is achieved. The incorporation of nucleotides which match the template DNA sequence in a complementary manner is performed by a polymerase 118, which binds to the DNA at the single-stranded/double-stranded junction. A self-assembled monolayer (SAM) 109 may be used to backfill the space next to and between DNA molecules 104, 105. The SAM-forming molecules feature a chemical head-group 108 for covalent coupling to the surface 107, and a variable tail group 111 which is used to facilitate steric and/or electrostatic interactions within the layer. For optimized steric and/or electrostatic interactions, the SAM may be a heterogeneous blend of molecules with different tail groups as indicated in FIG. 1. The use of a SAM which facilitates a rigid DNA alignment is an advantageous measure to provide for a reliable and improved sequencing, as described before and in the following.

In the following, further preferred or alternative aspects are explained, which may be incorporated at the sequencing apparatus of FIG. 1. In a preferred embodiment, working electrode 107 may be a conducting polymer, or a matrix layer containing dye molecules. Working electrode 107 can be a large singular conducting film, or alternatively, many individually addressable microelectrodes which are arrayed on a single substrate. Self-assembled monolayer 109 may be an alkane-thiol chain, with e.g. alkane chain-length=6. Also polyethylene glycol may be used. The chemical head-group 108 may be a group that contains one of—or a combination of—the following reactive groups: aldehyde, ketone, thiol, amine, carboxyl, hydrazine, hydrazide, hydroxyl, glycan, azide, alkyne, alkene, silicon, and any combination thereof. The variable tail group 111 may be e.g. a carboxylic or ethylene glycol moiety. In particular, the variable tail group 111 may also confer non-fouling properties, i.e. be protein-repellant. Linker 124 may be an alkane chain, with e.g. chain-length=6. Group 123 may contain one of—or a combination of the following reactive groups: aldehyde, ketone, thiol, amine, carboxyl, hydrazine, hydrazide, hydroxyl, glycan, azide, alkyne, alkene, silicon, and any combination thereof.

Furthermore, a capture oligonucleotide may be used for immobilization and a capture oligonucleotide may comprise, for example, 5 to 100 nucleotides. The primer nucleic acid 104 may comprise, for example, 5 to 100 nucleotides. The reinforcement oligonucleotide strand 105 may be an oligonucleotide of e.g. 5 to 100 nucleotides. The primer/adapter region may exemplarily comprise 5 to 100 nucleotides. Template oligonucleotide 100 is a single stranded DNA template with a length of for example, 5 to 10000 nucleotides. Label 117 may be a fluorescent dye molecule, like e.g. Cy3® or a colloidal semiconductor nanocrystal, like e.g. a colloidal CdSe quantum dot. The counter electrode 114 may be of gold, or indium-tin-oxide, or platinum. The standard voltage source 12 applies a typical voltage between 0 and −1.0 V to the working electrode. The applied voltage may depend on the dielectric characteristics like thickness and/or dielectric constant of the SAM spacer layer or any other dielectric layer in the system and may be significantly higher than −1.0 V if required. Positive potentials may also e applied. It is important to note that the applied voltage is used to polarize the surface, but not to drive any Faradaic currents (charge transfer) across the interface which would damage the molecular layer. The polymerase 118 may be Bst DNA polymerase from *Bacillus stearothermophilus*. Light emitting diode (LED) 116 may also be a laser, or a halogen or other lamp. The imaging optics 113 may comprise objectives, lenses, bandpass and dichroic filters, beam splitters, etc. Also a standard epi-fluorescence microscope, or a standard fluorescence imaging system as being used in commercially available systems for DNA sequencing may be used in combination with the sequencing apparatus 120 of FIG. 1. Moreover, a detector 110 like charge coupled device (CCD), or, photomultiplier, or photodiode detector may be used.

Exemplary Provision of a Vessel for Sequencing:

An exemplary embodiment of a vessel 119 may be produced by using the following, exemplary components. Commercial glass substrates are cleaned according to RCA procedures. Using standard optical lithography techniques, Au work 107 and Au counter 114 electrodes of 200 nm thickness are evaporated under vacuum onto the glass substrates, using a 10 nm thick Ti film as adhesion layer. Alternatively, PT and ITO can be used for the material of the electrode and/or the counter electrode. The electrode geometry can be adapted individually. Here we used circular working electrodes of 100 or 120 μm diameter, surrounded by large rectangular Au counter electrodes of mm dimensions. The electrode structures are sealed within a microfluidic channel made of elastomer and a top glass cover plate. A commercial epi-fluorescence microscope (Olympus) is used for generating the excitation signal 115 and detecting the fluorescence of Cy3® dyes 117 with an emission wavelength of ($\lambda$em~570 nm. The fluorescence of Cy3® dyes 117 are conjugated to the template DNA strand 100 or the polymerase 118. A green LED with an excitation wavelength of $\lambda$exc~530 nm is used as a light source and a standard photomultiplier with a single photon counting module for detection. Oligonucleotides 104 and 105 of mixed sequence are obtained commercially with standard (CH2)6-SH linkers 123, 124 for immobilization and pre-hybridized in Tris-buffered saline solution (10 mM Tris-buffer, pH 7.4, 200 mM NaCl, [oligo]=1 μM). After cleaning the Au surfaces with Piranha solution, the 104/105 duplexes are immobilized via their thiol groups on the Au surface by incubating the electrodes with 1 μM 104/105 oligo solutions in Tris-buffer for up to 1 h. Afterwards, the electrodes are washed with Tris-buffer and incubated with SAM forming reagent 109, i.e. 1 mM mercaptohexanol in Tris-buffer, for app./at least 5 minutes. Finally, the electrodes are washed with Tris-buffer and can be incubated with template DNA 100 (50 nM in Tris-buffer as used before, 15 min). Of course, also other buffers can be used.

Exemplary Sequencing Aspects

The unknown sequence of the single stranded DNA template 100 may be determined by carrying out the presented sequencing method in the following way. In particular, the pre-treatment steps may be applied before sequencing itself is carried out. First, a setup as provided e.g. in FIG. 1, may be prepared as described above, except for the DNA template to be sequenced 100. Second, the DNA-to-be-sequenced 100 may be fragmented into pieces of appropriate length by standard procedures like e.g. acoustic shearing. Depending on the maximally achievable read-length, this can be a few ten basepairs, a few hundred basepairs, or a few thousand basepairs, or even more. Third, adapter/primer sequences 106, which are complementary to the nucleic acid primer strand 104 on the surface, are ligated to the template DNA 100 using standard procedures. During this step, the template DNA may optionally be multiplied by PCR, if desired. Fourth, optionally, another adapter sequence may be appended on the opposing end of the DNA template. This can, for instance, be used to bind PL-emitter labeled oligos as has been described before with respect to FIG. 1. Fifth, the template DNA 100 with adapters/primers 106 is immobilized on the surface via hybridization to the primer strand 104 and the capture strand by using standard surface hybridization conditions. Sixth, a polymerase 118 is bound to the primer duplex 104/106 at the single-stranded/double-stranded junction.

Figure 2:
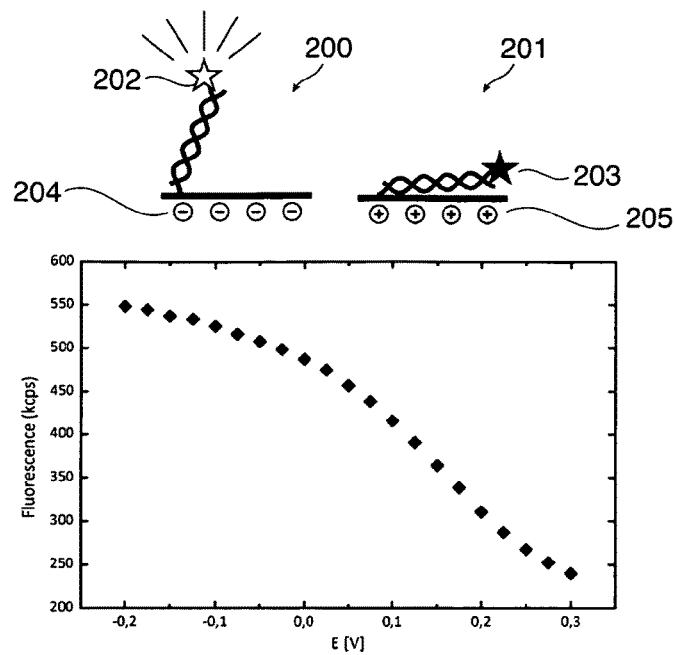

FIG. 2 shows a voltage response of a 40 base pair DNA layer and describes the principle of the distant dependent quenching mechanism used by exemplary embodiments of the present invention. FIG. 2 shows how end-tethered 40 bp DNA strands can be brought to an upright orientation by applying suitably negative voltages to the supporting electrode. Moreover, FIG. 2 schematically shows the dependency of the amount of quenching with respect to the distance of the label to the quenching medium. Exemplarily, the quenching medium is here embodied as the electrode to which the strand is attached. The label attached to the DNAs' upper ends approaches a maximal value when applying −0.2 V (vs. an ITO counter electrode, 50 mM NaCl solution). This can be explained when considering that (i) the negatively charged DNA is repelled from the negatively charged electrode surface, and (ii) that the non-radiative energy transfer from the label, depicted as a star, becomes weaker as the DNA's top end moves away from the PL-quenching layer. Taken together, this indicates an upright DNA orientation. In the lying configuration 201, in which the emission 203 is quenched due to the proximity of the label to the energy absorbing electrode, the signal intensity is low. In the standing configuration/orientation 200 the quenching is low as the distance between the label and the quenching medium is large. Therefore, the label emits with a high intensity 202. Signs 204 and 205 depict that by applying a negative field to the electrode the DNA strand is repelled and by applying a positive field to the electrode the DNA is attracted. The combination of the label and the quenching medium used herein are chosen, such that a non-radiative energy transfer from the excited label to surface plasmons in the quenching medium quenches the emission of the signal of the label when the label approaches the quenching medium, i.e. in a distant dependent manner. The diagram shown in FIG. 2 reflects the dependency of the observed/detected fluorescence of the label from applied voltage, which corresponds to the distance of the label to the quenching medium.

Figure 3:
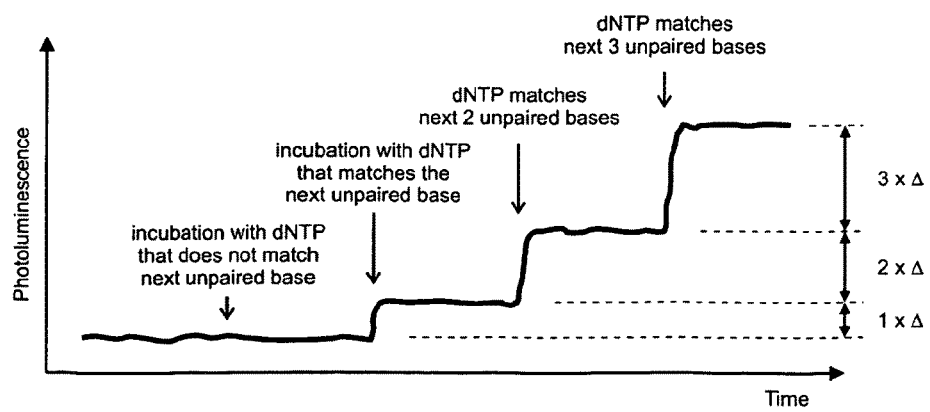

FIG. 3 shows an exemplary embodiment of the invention, in which a photoluminescence (PL) label is covalently or non-covalently associated with the template nucleic acid 100, as exemplarily described in the context of FIG. 1. In the following an exemplary embodiment of sequential scheme is presented in the context of FIG. 3. The PL-intensity 102 of the PL label 117 is continuously measured over time, which can be gathered from FIG. 3 (step 1). Optionally, a negative voltage to repel the negatively charged DNA from the surface may be applied to the working electrode (step 2).

The surface is incubated with a solution containing one type of nucleotide (e.g. dATP), (step 3). If the dNTP is complementary to the upcoming unpaired nucleotide along the template DNA next to the single-stranded/double-stranded junction, it will be incorporated by the polymerase, as shown in FIG. 1 with sign 118. Consequently, the PL-intensity will increase by a characteristic value ΔPL, as can be seen from the PL plot in FIG. 3. The reasons may be the following. In case of using a PL-labeled polymerase, as exemplified in FIG. 1a, the polymerase extends the double-stranded portion of 100/104 and moves away from the quenching surface by the distance of one base-pair spacing for every incorporated dNTP. The base pair spacing is approximately 0.34 nm. For the following FIGS. 5 and 6 this means, h(n+1)=h(n)+0.34 nm. As the distance h between the polymerase-bound PL-label and the quenching layer increases, the non-radiative energy transfer decreases, and thus the PL emission increases by ΔPL.

In case of a PL-labeled DNA, as exemplified in FIG. 1b, the polymerase extends the double stranded portion of 100/104 and thereby the fixture point, i.e. the junction, of the flexible single stranded portion of the template DNA 100 moves away from the surface, see FIGS. 5 and 6. We note that the position of the PL-label 117, respectively, is not absolutely fixed in space, but may be subjected to Brownian fluctuations of the flexible single stranded DNA segment. However, this does not harm the present invention. Hence, the measured PL intensity corresponds to a time-averaged height h of the PL-label above the quenching layer. As the vertically aligned, double-stranded DNA segment becomes extended, the fixture point of the single-stranded segment moves upward; this effectively translates to an increase in the time-averaged height of the PL-label, which can used by the present invention to detect the incorporation event.

If, due to a stretch of homo-nucleotides along the template DNA, the dNTP is incorporated multiple times, the PL intensity increases by a corresponding multiple of ΔPL (2×ΔPL, 3×ΔPL, etc.) as shown in FIG. 3. If the dNTP is a mismatch, the PL intensity remains unchanged, cf. FIG. 3. Further, dNTP which has not been incorporated is removed by exchanging the solution with dNTP-free buffer (step 4). The previous steps 2 to 4 are repeated with a different type of nucleotide (e.g. dCTP, dGTP, dTTP) (step 5). Moreover, steps 2 to 5 are repeated until the PL-intensity does not change for any type of dNTP anymore, that is, the whole template DNA strand has been converted from a single- to a double-strand. Thus, the user is provided with the complete sequence of template 100. The signal 102 can be used by the sequencing apparatus for detecting each incorporation of the dNTP into the template nucleic acid 100 based on a change of the observed signal Δ, or 2Δ, or 3Δ . . . , wherein the change of the signal results from a change of a distance 103 of the label to the quenching medium caused by the incorporation of the dNTP.

Figure 4:
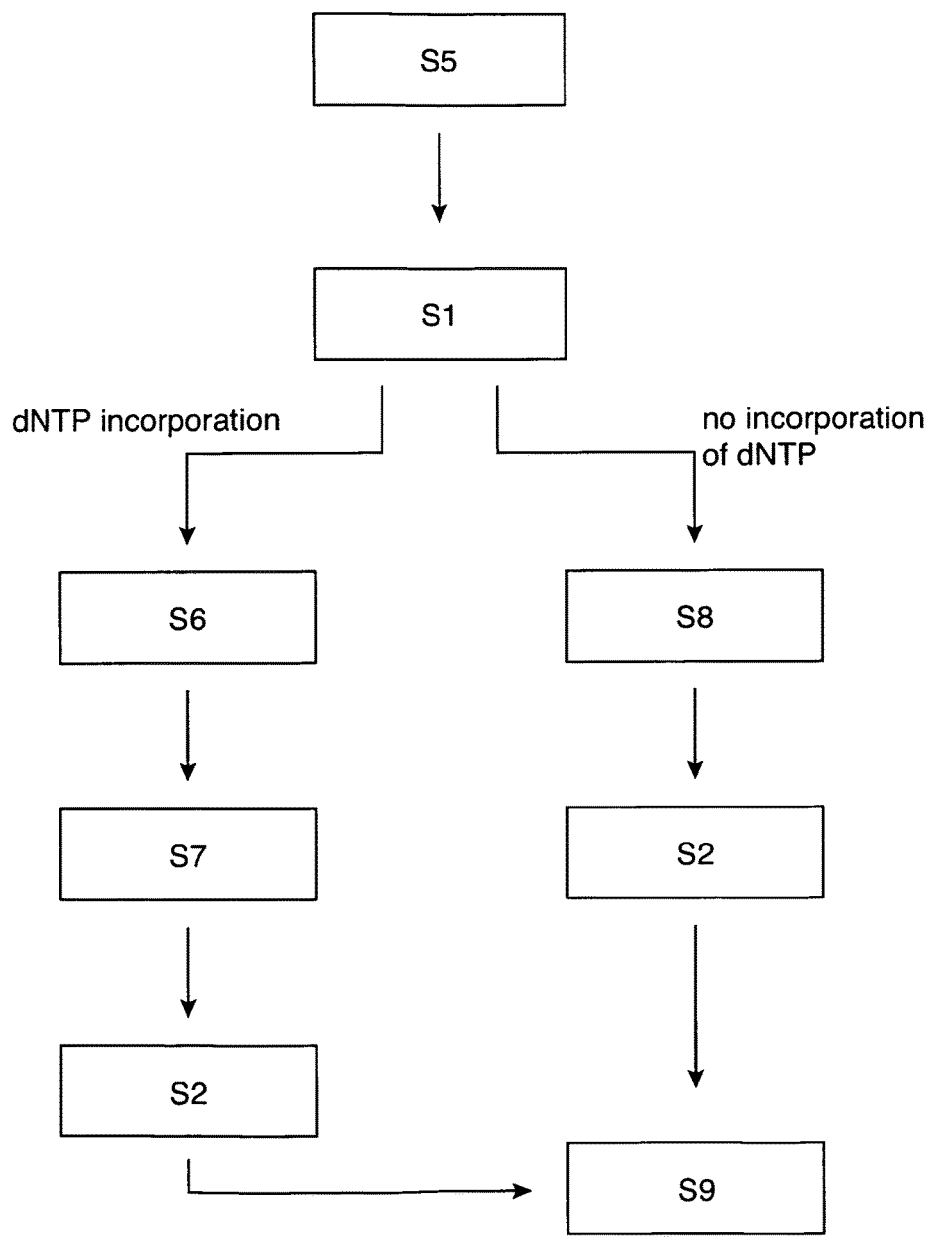

FIG. 4 shows a flow diagram of a sequencing method according to an exemplary embodiment of the invention. A method for sequencing a template nucleic acid is shown, which is immobilized on a substrate, wherein a label is covalently or non-covalently associated with the template nucleic acid and wherein a nucleic acid primer is annealed to said template nucleic acid. Further, a quenching medium for quenching a signal of the label is provided. The method comprises the step of incubating the substrate with a solution containing a plurality of nucleotides of a first type S5. This may be seen as the step of adding a nucleotide. Moreover, the step of observing a signal of the label at least before and after the adding of the nucleotide is shown with S1. In a first case, in which the first type of the dNTP is complementary to an upcoming unpaired nucleotide along the template nucleic acid next to a single-stranded/double-stranded junction, the nucleotide of the solution is incorporated into the template nucleic acid in step S6. The first case is shown on the left in FIG. 4. In the first case an increase of the signal due to the incorporation of the nucleotide is detecting in step S7, wherein the change of the signal results from a change of a distance of the label to the quenching medium caused by the incorporation of the nucleotide into the template. In the second case, in which the first type is not complementary to the upcoming unpaired nucleotide and in which the nucleotide is not incorporated, an unchanged signal is detecting in step S8. In both cases, the observed signal of the label is used for detecting an incorporation of the nucleotide into the template nucleic acid based on a change of the observed signal in step S2. If desired, steps S5 to S2 can be repeated with a different or the same type of nucleotide during step S9. Consequently, the method determines whether said nucleotide is incorporated or not incorporated at a 3'-end of said nucleic acid primer annealed to said template nucleic acid.

FIG. 5 shows sequencing of a DNA strand that is labeled with a photoluminescence label according to exemplary embodiments of the invention. FIG. 6 shows sequencing with a polymerase that is labeled with a photoluminescence label. A change of the distance 103 of the label 117 to the quenching medium 107 is caused by the incorporation of a nucleotide 501 or 601 in FIGS. 5 and 6. The adding of the nucleotide is depicted with signs 500 and 600. The base pair spacing between bases in the template 100 is approximately 0.34 nm. In both FIGS. 5 and 6 the height h of a strand comprising the template 100 and the primer 104 having n nucleotides is h (n). Thus, after the incorporation of one matching nucleotide dNTP the height is h (n+1). Hence, h(n+1)=h(n)+0.34 nm. As the distance h between the polymerase-bound label and the quenching layer increases, the non-radiative energy transfer decreases, and thus the signal intensity emission changes by a Δ of the intensity.

Figure 7:
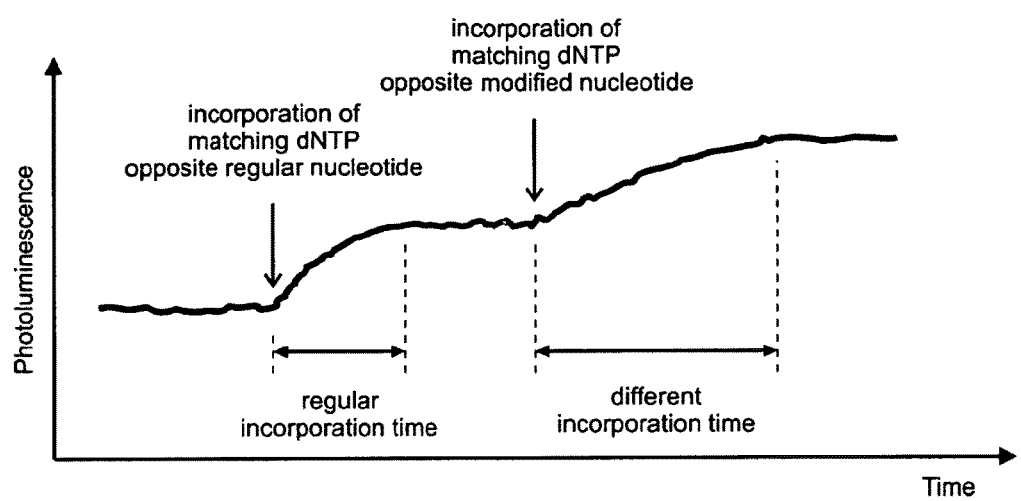
FIG. 7 shows a time-dependent photoluminescence signal during nucleotide incorporation in an ensemble measurement of a sequencing method according to an exemplary embodiment of the invention.

FIG. 7 shows a time-dependent photoluminescence signal during nucleotide incorporation in an ensemble measurement according to an exemplary embodiment of the invention. FIG. 7 relates to the aspect of nucleotide incorporation rates and the discrimination of modified nucleotides. The incorporation rate of the different dNTPs can be determined by following the polymerase-mediated extension of the double-stranded DNA segment in, for example, a real-time PL measurement as shown in FIG. 7. The steady PL increase between dNTP incubation and signal saturation depends on the dNTP concentration, which can be adjusted according to the sampling time of the used PL detection setup. Importantly, this also depends on the processivity of the polymerase for the respective dNTP. In the rate-limited reaction regime, the signal change follows an exponential time-course PL~exp(−kdNTP×t), where kdNTP is the incorporation rate of the polymerase for a given dNTP. This dNTP-specific incorporation rate can be used to discriminate different dNTPs according to the presented embodiment. In particular, measuring the characteristic incorporation rate, or, conversely the incorporation time constant, enables one to discriminate whether nucleotides along the template DNA strand have been chemically modified, for instance if they have been methylated in the course of an epigenetic process, or have been otherwise damaged. This is due to the fact that the processivity of polymerases generally depends on the chemical structure of the nucleotide to-be-incorporated, and the chemical structure of the corresponding unpaired nucleotide on the template DNA strand. The presented method makes use thereof. The apparatus for sequencing disclosed herein is configured to detect whether a regular incorporation time was observed or whether a different incorporation time was observed. If desired, a comparison with default incorporation times can be carried out.

Moreover, by measuring the incorporation time constant it is also possible to determine how often the solute dNTP has been incorporated into the DNA strand, i.e., to gauge the length of homo-nucleotide stretches along the template. We found experimentally that the incorporation time scales with the number of nucleotides within a homo-nucleotide segment. In addition to measuring the absolute change in signal intensity (see ΔPL in e.g. FIG. 3), a measurement of the incorporation time provides complementary information on the length of a homo-nucleotide segment, which improves the accuracy of the determination. The presented method makes also use of this insight.

The measurement modalities described above can be applied to the investigation of (A) ensembles of DNA template clones and (B) single molecules.

(A) For ensemble measurements, many, e.g. up to billions of monoclonal DNA colonies, so called "polonies", can be generated on a single surface by established procedures, for instance by the bridge amplification method or similar methods. Typical measurement signals are depicted in FIGS. 3 and 7.

(B) For the sequencing of single DNA molecules, capture oligos are immobilized on the electrode surface at extremely low density, so that the distance between two adjacent DNAs is greater than the lateral spatial resolution of the optical imaging system (typically ~0.5 μm). In practice this can be accomplished by (i) using a very dilute oligonucleotide concentration in the immobilization solution, and/or (ii) employing electrical means to dilute the DNA density on the surface as described in previous work, and/or (iii) using very small electrode structures of sub-micron lateral dimensions which can accommodate a single DNA molecule only.

The single molecule measurement requires the use of stable PL-labels, which are not prone to photobleaching. Thus, the use of non-bleaching semiconductor nanocrystals or highly photo-stable organic fluorophores may be preferable. Labeling with multiple PL-labels is also possible. In addition, the photobleaching stability is increased by the quenching gold layer.

Based on observed data as shown in FIG. 7, the following steps can be carried out by an embodiment of the present invention. Determining a time averaged signal emitted by the label, i.e. step S3, comparing the time averaged signal with a signal of a point in time before the incubation, i.e. step S4, and wherein previously described step b) of determining is carried out based on a result of the comparison.

FIG. 8 schematically shows nucleotide incorporation on a single molecule level. The PL-trace of a single molecule measurement is shown in FIG. 8. In contrast to the steadily increasing signals observed in ensemble measurements of FIG. 7, the incorporation of a matching dNTP results in a sudden jump of the PL intensity by a characteristic ΔPL value in the single molecule case. The time span between pumping the dNTP solution across the surface, i.e. the incubation start, and the actual jump in PL intensity reflects the incorporation time of a single dNTP into a single DNA template. It is a stochastic variable with an expectance value that corresponds to the ensemble incorporation time, $t-1 = conc_{dNTP} \times k_{dNTP}$. In analogy to the above discussion of the incorporation rate determination in ensemble measurements, the presence of a different, i.e. chemically modified, nucleotide may be inferred from the single molecule incorporation time span. However, due to the stochastic nature of a single dNTP incorporation, the discrimination of two different nucleotides from their different single molecule incorporation times can only be made with reasonable certainty if the expectance values for the incorporation times differ significantly, i.e. by more than an order of magnitude. The apparatus for sequencing disclosed herein is configured to detect such a differing.

In the following, aspects regarding the determination of polymerase association and dissociation rates are explained. The previously described experimental setup comprising the sequencing apparatus and the vessel allows for the determination of the association rate constant $k_{on}$ and dissociation rate constants $k_{off}$ of a polymerase and a DNA sequence. In the following, the association rate constant $k_{on}$ and dissociation rate constants $k_{off}$ of a polymerase and a DNA sequence are depicted in the diagram:

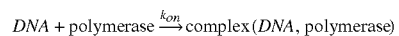

To this end, the signal intensity is recorded over time. According to case a in FIG. 1, the signal intensity increases from zero intensity or a background intensity when a polymerase binds to the DNA primer region due to the presence of the label on the polymerase. The kinetic rate constants can be determined by fitting analytical interaction models to the time-resolved association- and dissociation-curves, and affinity constants can be determined either from the analyzed rate constants $K_a = k_{on}/k_{off}$ or by concentration dependent titrations. The sequencing apparatus presented herein, e.g. the provided calculation unit, may carry out this method accordingly.

FIG. 9 shows incubation of surface-immobilized double-stranded DNA sequence (FIG. 9a) with a 3-nucleotide single-stranded overhang with mismatching dNTPs (FIG. 9b) and matching dNTPs (FIG. 9c) in accordance with an exemplary embodiment of the invention. In the following more experimental data corroborating the described invention will be described. The data of FIG. 9 pertain to the case depicted in FIG. 1b, i.e., detection with a labeled DNA strand. Commercially obtained Bst DNA polymerase from New England Biolabs was used as the polymerase. However, this is only an exemplary embodiment. FIG. 9 shows data for a mixed random DNA sequence featuring 42 basepairs with a 3 nucleotide, i.e. TTT, single-stranded overhang at the surface distal end. The DNA 104 and 105 was pre-hybridized in solution and afterwards bound to the surface via two . . . -(CH2)6-SH linkers 123 and 123 using mercaptohexanol (HO-(CH2)6-SH) as a SAM 109. Protocols have already been described here before. As label and emitter 117 the fluorophore Cy3 was used. As a negative control, the surface was incubated with 1 μM dGTP (FIG. 9b). As G cannot form a basepair with the first unpaired nucleotide T (at position 43), the Cy3 fluorescence intensity stays constant, that is, G is not incorporated and the dsDNA segment is not extended. When the surface-immobilized DNA is incubated with 1 μM dATP (FIG. 9c), which is the matching complementary nucleotide for the 3 unpaired T's at positions 43, 44, 45, the fluorescence increases strongly by +31%. This increase is attributed to the incorporation of 3 A's and the extension of the dsDNA segment by 3 basepairs. The fluorescence increase supports the scheme depicted in FIG. 5 and has already been explained herein before. The solid line is a single exponential fit, which in agreement with the scheme depicted in FIG. 7 yields an incorporation rate constant $k_{dATP}=(0.029\pm0.001)$ s$^{-1}$.

Consequently, based on FIG. 9, it is a method provided which observes the signal of the label at least before and after the adding of the nucleotide and uses the observed signal of the label for detecting the incorporation of the nucleotide into the template nucleic acid based on the change of the observed signal of the label. Therein, the change of the signal results from a change of a distance of the label to the quenching medium caused by the incorporation of the nucleotide into the template nucleic acid.

FIG. 10 shows the incorporation of a single dNTP in accordance with an exemplary embodiment of the invention. FIG. 10 shows data of the incorporation of a single nucleotide into a DNA construct analogous to FIG. 9a, but with a 15 nucleotide single-stranded overhang. Upon incubation with 1 µM dGTP solution (at t~1.2 min) the Cy3-fluorescence increases by +12%. This fluorescence increase corresponds to one third of the fluorescence increase observed for the incorporation of three dNTPs in FIG. 9C, which is +31%. This supports the scheme depicted in FIG. 3, namely, that the magnitude of the PL change scales with the number of incorporated nucleotides.

FIG. 11 shows the polymerisation of a 25 nt single-stranded segment along a 45 nt DNA sequence by incubation with a mixture of all 4 dNTPs (FIG. 11b) or the sequential incubation with matching dNTPs (FIG. 11c) in accordance with an exemplary embodiment of the invention. FIG. 11 shows the incorporation of 25 nucleotides into the 45 nucleotide DNA sequence listed in FIG. 11a. When incubating the DNA with a 1 µM mixture of dATP & dGTP & dCTP & dTTP, a very pronounced fluorescence increase is observed if the DNA is tethered to the surface with TWO (CH2)6-SH linkers (termed "double-SH-DNA" in FIG. 11b), while the fluorescence increase incurred for DNA tethered with only linker (termed "single-SH-DNA" in FIG. 11b) is much less prononounced. This confirms that by using two linkers the DNA is efficiently aligned in a vertical orientation. FIG. 11c shows the fluorescence change when sequentially incubating the immobilized DNA with 1 µM solutions of A (#=1), T, A, G, A, G, T, G, A, T, G, T, A, C, G, A, G, A, T, A (#=20). The fluorescence increase incurred for each step is approximately linearly proportional to the number of incorporated nucleotides. Note also that injections #3, #13, and #20 led to the incorporation of multiple nucleotides due to homo-nucleotide stretches along the template DNA, which can be detected by the presented method and apparatus.

Figure 12A:
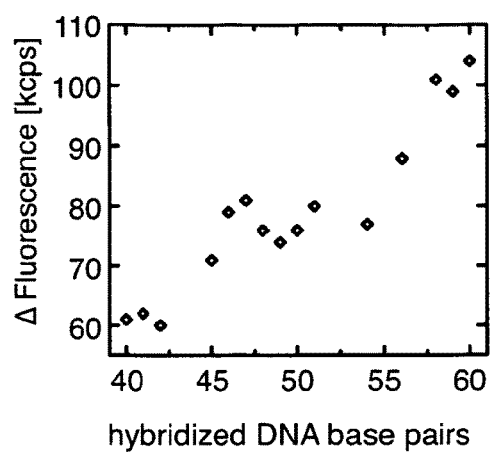

In the following, advantages of the alignment means provided by the present invention will be explained. In particular, the advantage of using more than one linker and/or other means to lock the DNA alignment is not obvious to an average researcher who is proficient in the field, as we ourselves tried to work with DNA which was tethered by one linker at first. However, in certain scenarios and with certain setups these experiments may produce sequencing data, as FIG. 12a shows, which at a first glance seem to be hardly interpretable. When sequentially incorporating matching nucleotides to a DNA sequence which was analogous to the one listed in FIG. 11a, but featured only one instead of two linkers, the PL signal increased in a hardly predictable way but exhibited a modulated behavior, see FIG. 12a. We were able to explain this behavior by devising a "helical-turn" model, which will be explained in the following.

Figure 12B:
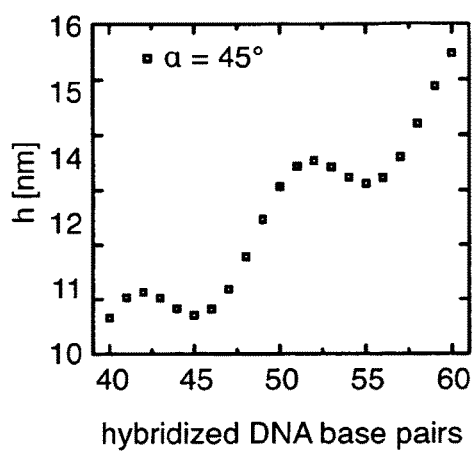

Given that the DNA is only tethered to the surface by one of its strands, it remains free to rotate around this pivot point by Brownian motion. As a consequence of this degree of freedom (and the associated entropy, the average DNA orientation adjusts to a low DNA-surface angle between 30° and 50°, that is a quite tilted orientation. In this case, the height increase of the DNA's top end to the surface upon incorporation of nucleotides does not only depend on the extension of the dsDNA length, but is superimposed by the helicity of the DNA structure. For every ten incorporated nucleotides, the DNA structure makes a full helical turn. The height h of a label attached to the DNA's top end may be calculated as a function of the number of incorporated nucleotides n using the equation:

$$h = 2\cdot\cos\alpha + n\cdot 0.34\cdot\sin\alpha - \left[1-\cos\left(n\cdot\frac{2\pi}{10}\right)\right]\cdot\cos\alpha$$

which is plotted in FIG. 12b and resembles the experimental data of FIG. 12a. The complexity of this unexpected mechanism makes it impossible to extract unambiguous sequence information from these data without having the helical turn model provided herein. Thus, it underlines the advantage of using a rigid linker structure and/or other means to facilitate a defined vertical DNA orientation, as have been presented herein before and will be disclosed hereinafter.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. A single processor or other unit may fulfill the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A method for sequencing a template nucleic acid immobilized on a substrate, wherein a label is covalently or non-covalently associated with the template nucleic acid,
    wherein a nucleic acid primer is annealed to said template nucleic acid,
    wherein a quenching medium for quenching a signal of the label is provided,
    wherein the quenching medium is a quenching layer,
    the method comprising at least the steps of:
    a) providing the label at a height h1 at the template nucleic acid,
    b) adding a nucleotide, wherein the nucleotide is unlabeled,
    c) incorporating the nucleotide into the template nucleic acid thereby causing a change of the height of the label from a height h1 to a height h2 above the quenching medium,
    d) recording the change of the signal of the label based on the change from the height h1 to the height h2, e) determining whether said nucleotide is incorporated or not incorporated at a 3'-end of said nucleic acid primer annealed to said template nucleic acid by:

observing a signal of the label at least before and after the adding of the nucleotide using the observed signal of the label for detecting an incorporation of the nucleotide into the template nucleic acid based on a change of the observed signal of the label, and wherein the change of the signal results from a change of a distance of the label to the quenching medium caused by the incorporation of the nucleotide into the template nucleic acid.

2. The method according to claim 1, further comprising step f) wherein f) comprises repeating steps a) - e) to determine a full sequence of said template nucleic acid.

3. The method according to claim 1, the method further comprising the step immobilizing the template nucleic acid on the substrate via a capture nucleic acid.

4. The method according to claim 3, wherein the capture nucleic acid is a double stranded capture nucleic acid having a first strand end and a second strand end, and the method further comprising the step immobilizing the double stranded capture nucleic acid on the substrate by means of a first chemical linker at the first strand end and by means of a second chemical linker at the second strand end.

5. The method according to claim 3, the method further comprising the step aligning the capture nucleic acid in a desired angular configuration with respect to a surface of the substrate by applying a force onto the capture nucleic acid.

6. The method according to claim 5, wherein the force onto the capture nucleic acid is provided by applying a DC voltage between an electrode on the substrate and a counter electrode.

7. The method according to any of the preceding claims, the method further comprising the step providing co-adsorbed molecules on the substrate beside the capture nucleic acid for sterically repelling the template nucleic acid and / or the capture nucleic acid.

8. The method according to claim 1, the method further comprising the step, quenching the signal of the label by the quenching medium.

9. The method according to claim 1, the method further comprising the steps determining a time averaged signal emitted by the label, comparing the time averaged signal with a signal of a point in time before the incubation, and wherein step the b) of determining is carried out based on a result of the comparison.

10. The method according to claim 9, the method further comprising the step reducing an amount of the quenching upon the incorporation of the nucleotide into the template nucleic acid thereby increasing the signal which is emitted by the label.

11. The method according to claim 1, the method further comprising the steps incubating the substrate with a solution containing a plurality of nucleotides of a first type incorporating the nucleotide of the solution into the template nucleic acid in a first case, in which the first type is complementary to an upcoming unpaired nucleotide along the template nucleic acid next to a single-stranded/double-stranded junction, in the first case detecting an increase of the signal due to the incorporation of the nucleotide or, in a second case, in which the first type is not complementary to the upcoming unpaired nucleotide and in which the nucleotide is not incorporated, detecting an unchanged signal, and repeating the above steps with a different type of nucleotide.

12. The method according to claim 1, the method further comprising the step determining a nucleotide incorporation rate or a nucleotide incorporation time based on a time development of the signal emitted by the label during the incorporation of the nucleotide.

13. The method according to claim 12, the method further comprising the steps comparing the determined nucleotide incorporation rate with a default nucleotide incorporation rate or comparing the determined nucleotide incorporation time with at least one default nucleotide incorporation time, and determining the type of the nucleotide based on a result of the comparison.

14. The method according to claim 12, the method further comprising the steps comparing the determined nucleotide incorporation time with at least one default nucleotide incorporation time, and determining a chemical state of the template nucleotide, for example a methylated state of the template nucleotide, based on a result of the comparison of the nucleotide incorporation times.

15. The method according to claim 12, wherein the method is carried out on a chip, the method further comprising the steps incubating the chip with a solution comprising a plurality of nucleotides of a first kind, and gauging a length of a homo-nucleotide stretch along the template nucleic acid based on the determined nucleotide incorporation rate.

* * * * *